United States Patent [19]

Redding, Jr.

[11] Patent Number: 5,455,342
[45] Date of Patent: Oct. 3, 1995

[54] METHOD AND APPARATUS FOR THE MODIFICATION OF STARCH AND OTHER POLYMERS

[76] Inventor: Bruce K. Redding, Jr., 2708 S. 86th St., Philadelphia, Pa. 19153

[21] Appl. No.: 119,995

[22] Filed: Sep. 10, 1993

Related U.S. Application Data

[63] Continuation-in-part of Ser. No. 871,081, Apr. 20, 1992, abandoned.

[51] Int. Cl.⁶ ............................................. C08B 37/00
[52] U.S. Cl. ........................ 536/102; 536/114; 523/340; 523/342
[58] Field of Search ..................... 536/102, 114; 523/340, 342

[56] References Cited

U.S. PATENT DOCUMENTS

| | | | |
|---|---|---|---|
| 2,929,748 | 3/1960 | Schwandt | 536/102 |
| 3,067,067 | 12/1962 | Etheridge et al. | 536/102 |
| 3,169,083 | 2/1965 | Taylor | 536/102 |
| 3,220,884 | 11/1965 | Huber et al. | 536/102 |
| 3,276,907 | 10/1966 | Huber et al. | 536/102 |
| 3,527,606 | 9/1970 | Taylor et al. | 536/102 |

OTHER PUBLICATIONS

Webster's II New Riverside University Dictionary, Riverside Publishing Co. Houghton Mifflin Co. 1988 p. 915.

*Primary Examiner*—Nathan M. Nutter
*Attorney, Agent, or Firm*—Robert S. Lipton; Lipton & Stapler

[57] ABSTRACT

A method and apparatus for the modification of the physical properties of polymers through pressure processing techniques. The apparatus is comprised of a piston device which acts on the polymer substrate charged within the confines of a compression chamber. The piston delivers an abrupt pressure change to the substrate for the purpose of effecting the desired modification of physical properties including altered thermal, viscosity, solubility, turbidity and hardness profiles. Predictable characteristics may be imparted to the substrate through variation of pressure duration and intensity as well as the number of piston strokes applied. Modification of the physical properties of starch and gum arabic, in particular, is disclosed.

1 Claim, 18 Drawing Sheets

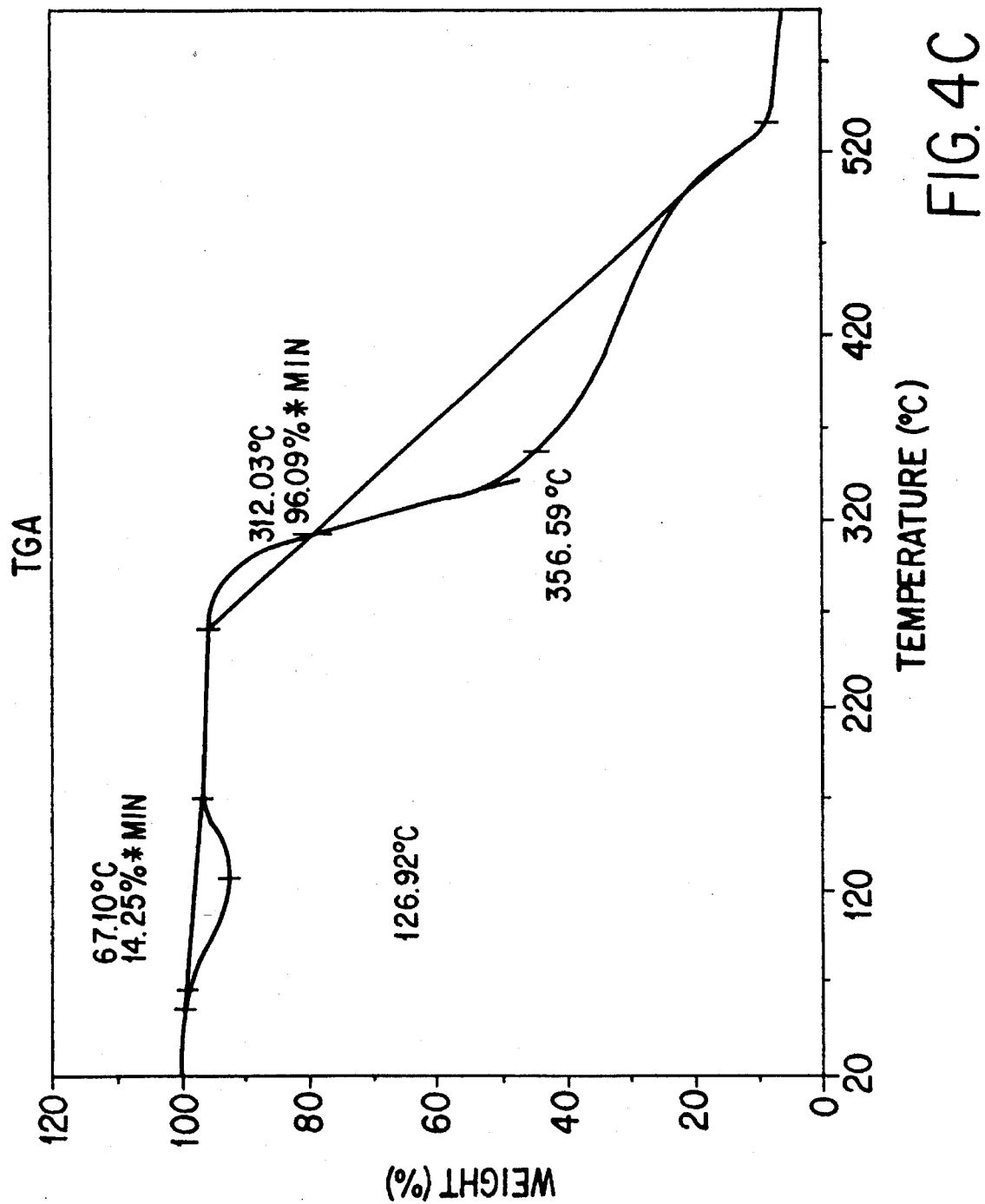

METHOD AND APPARATUS FOR THE MODIFICATION OF STARCH AND OTHER POLYMERS

This is a continuation-in-part of U.S. patent application Ser. No. 07/871,081 filed Apr. 20, 1992, and now abandoned.

FIELD OF THE INVENTION

The subject invention relates to a method and apparatus for the physical modification of polymers in general, and to the production of novel starch compositions through the use of pressure processing techniques, in particular.

BACKGROUND OF THE INVENTION

Starch, a natural polymer $(C_6H_{10}O_5)_n$ derived from plant materials, is commonly found in the form of tiny microscopic granules (5–25 microns in diameter) comprised of stratified layers of starch molecules formed around a hilum nucleus. The starch granule shape may be round, oval or angular, and consists of a radially oriented crystalline aggregate of two anhydrous D-glucose polymers: amylose and amylopectin. The former is a straight chain polymer of several hundred glucose units linked by alpha-1-4-glycosidic linkages. Amylopectin is a branched polymer of several thousand glucose units with alpha-1-6-glycosidic linkages at the branched points and alpha-1-4 linkages in the linear regions. Individual branches may have between 20–30 glucose residues.

Heretofore, physical and chemical modification of starch has been accomplished through a variety of processes in order to realize improved performance characteristics in the food, paper, textile and pharmaceutical industries. For example, improved rheological and thermal stability properties of modified starches result in superior frozen, instant, dehydrated, and heat and serve food products which would not otherwise be economically competitive. Similarly, in the pharmaceutical industry, solubility and hardness properties of starch excipients are improved to effect the appearance and performance of tablets. Other physical properties of starches important to formulators and food processors today include viscosity, acid stability, moisture resistance or affinity, gel characteristics, decomposition rates (shelf life), shear resistance, texture, mouth feel and clarity when in solution.

Modification of starch is conventionally accomplished through thermal or chemical means. Pregelatinization, for example, is the pre-cooking of starch and starch products to make them cold water soluble. This solubility property, more commonly referred to as "cold water swelling", finds utility in instant foods such as puddings, pie fillings, analogues, and textured products. Pre-cooking is accomplished by application of a starch slurry to a steam-heated roll where the starch is cooked instantly and dried. Thus, pregelatinized starches are those which have been hydrated and treated thermally. Through moisture and heat treatments the crystallinity of several starch products can be modified to provide desired property changes.

Starch may also be modified chemically by a process known as crosslinking to provide inhibition properties. Bi- or polyfunctional reagents such as phosphorus oxychloride are used to covalently bridge, or crosslink, two starch molecules at various locations along their chains to provide viscosity stability as well as acid, heat and shear tolerance. These properties find utility in acid foods (salad dressing and pie fillings), canned foods, gravies and sauces, cream-style corn, and oriental foods.

Another chemical modification process of starch is substitution. Here, the introduction of substituent groups on starch by treatment with monofunctional reagents which react with the hydroxyl groups on starch produces starch esters and starch ethers. Treating substituents include acetate, succinate, phosphate, hydroxypropyl, and octenylsuccinate. The primary purpose of substitution is to impart resistance to retrogradation and gelling of amylose and eliminate the association of the linear segments of amylopectin at low temperature. Other effects of this process include a lowering of gelatinization temperature, increased viscosity, improved colloidal properties, and modification of hydrophilic or hydrophobic character.

Still other chemical modification processes such as acid hydrolysis and oxidation may be employed to impart low hot paste viscosity, high alkali number, a high ratio of cold to hot paste viscosity, color changes, and high adhesive and binding powers to the starch composition. Starches so chemically modified find utility in the manufacture of gum candy and as coating agents for confections and breaded foods.

Each of the above modification processes, however, suffer from various shortcomings and result in starch products with physical property limitations. In the field of pharmaceuticals starch is frequently used as a binder for active ingredients and as a disintegrant upon contact with water or gastric solutions. Pregelatinized corn starch provides tablets with hardness properties in the range of 1 to 4 Kp. Present demands, however, require hardness levels in the range of 10–14 Kp, an expectation which starch modified by prior art methods simply can not meet. While the use of starch in tableting formulations is still common practice, problems of uniformity between modified batches and a demand for tablets of greater hardness resulted in its departure from the status of a preferred pharmaceutical excipient.

Prior art methods of chemical starch modification are also inherently cost in-effective requiring the additional expense of crosslinking chemicals or functional reagents to produce the desired physical characteristics in the substrate. Disposal problems associated with unwanted reaction by-products further adds to cost and environmental concerns. Also, chemical modification methods yield product in batch quantities, rather than on a continuous or semi-continuous basis and, therefore, are less time efficient. Production rates are further diminished when more than one chemical modification must be made to the starch substrate to yield a product with all of the desired characteristics. Moreover, the starch end-product itself often suffers from other limitations similar to the deficient tablet hardness profiles, discussed above. Inferior viscosity, shear resistance and thermal profiles of the starch end-product, for example, may frustrate the performance of products incorporating starch modified by prior art means.

It is clear that a need exists for a method of modifying the physical properties of starch and other polymer compositions to provide improved performance characteristics useful in the food, pharmaceutical and other industries. The subject invention completely obviates all of the above described shortcomings by providing a method and apparatus for the physical modification of polymers such as starch by pressure processing techniques; the modified novel end-products themselves being characterized by improved physical properties.

SUMMARY OF THE INVENTION

Applicant has discovered that the application of pressure to starch and other polymers as herein described results in the immediate conversion of the substrate to a form possessing modified physical properties.

A liquid substrate composition characterized as either a solution, slurry, dispersion, emulsion, mixture, suspension, or other substance exhibiting fluid dynamics, is treated by a piston apparatus wherein extreme heat and force are transmitted to the substrate resulting in its modification.

More particularly, the apparatus is comprised of a piston device which acts on the substrate charged within the confines of a compression chamber. The piston delivers a number of abrupt pressure changes to the substrate for the purpose of effecting the desired modification of physical properties. Specific predictable characteristics may be imparted to the substrate through variation of pressure duration and intensity as well as the number of piston strokes applied. It is theorized that the abrupt pressure changes also produce cavitation effects which aid in the modification process.

Accordingly, it is a primary object of the subject invention to provide a novel method and apparatus for affecting physical modifications in substrates.

It is another primary object of the subject invention to provide a method and apparatus for inducing changes in the physical properties of substrates.

It is also a primary object of the subject invention to provide a superior starch composition characterized by superior thermal, viscosity, solubility, turbidity and shear resistent properties.

Another object is to provide a method and apparatus for physically modifying a substrate and its physical properties through the application of one or more abrupt pressure changes to the substrate.

Another object is to provide a method for physically modifying a substrate and its physical properties through the application of at least one abrupt pressure change as produced by a piston apparatus.

An additional object is to provide a method and apparatus capable of modifying a substrate and its physical properties almost instantly upon exposure to one or more abrupt pressure changes.

Yet another object is to provide a cost effective and energy efficient method of physical modification of starch and other substrates without the necessity of chemical additives required by prior art processes.

Still another object is to provide a method for physically modifying a substrate and its physical properties which can be carried out on a semi-continuous basis.

With the above and such other objects in view as may hereafter more fully appear, the subject invention is comprised of the novel construction and combination of apparatus components, methods of their operation and resulting products as may be more fully appreciated upon reference to the accompanying drawings.

BRIEF DESCRIPTION OF THE DRAWINGS

FIG. 4 shows the Thermographic analysis of various Capsul starches.

FIG. 4C shows the TGA spectra of Capsul starch which has been dissolved into a solution, pressure treated by the apparatus depicted in FIG. 1 at setting 90 for 20 re-cycle treatments and then vacuum dried into a dry powder.

DETAILED DESCRIPTION OF THE PREFERRED EMBODIMENT

The discovery which is the subject of this invention is that the treatment of starch by piston strokes results in the modification of the substrate's physical properties. Reference is now made to FIG. 1 wherein a perspective view of the preferred embodiment of the subject apparatus is illustrated. The device as shown is comprised of a converted air-operated hydraulic pump with piston means for generating an abrupt pressure change to a target substrate 40 which is pumped through the apparatus.

Figure 2A:
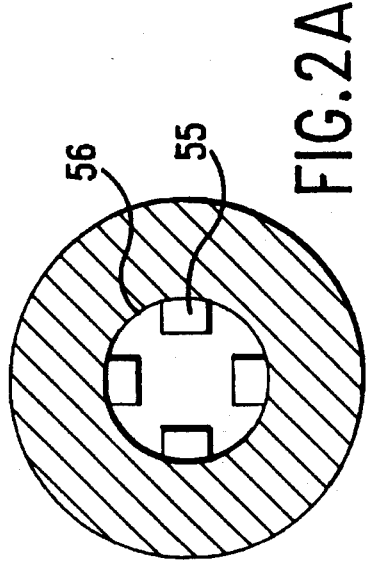
FIG. 2A is a schematic diagram of the baffled chamber component of the pressure treatment apparatus.

A reservoir 5 is provided as a receptacle for the substrate 40 and may be adapted with a stirrer and heating coils (not shown) where necessary to maintain homogeneity and flow properties. Reservoir 5 is mounted to transfer conduit 6 which leads to pressure application assembly 2. Transfer conduit 6 may also be heated with heating coils to maintain the temperature of the substrate 40 as it passes to piston assembly 2. Piston assembly 2 comprises compression chamber 1, the terminal end of which is disposed between inlet valve 3 and outlet valve 4, and piston housing 42 which has within it movable piston 20 (FIG. 2A). A series of seals and gaskets designated reference numerals 21 and 50 are placed along compression chamber 1 to isolate the substrate 40 from the balance of the piston assembly 2. Valves 3 and 4 may be solenoid, manually operated or automatic check valve devices. Movable piston 20 is displaced within housing 42 by motor 22 which may be hydraulic, pneumatic, electric or combustion powered. Output transfer conduit 7 is connected to exit valve 4 and leads to a separate baffled chamber 23 (FIG. 2A).

Two modifications of the subject apparatus may be employed to regulate the closing of output valve 4. First, output transfer conduit 7 may be of significantly lower inner diameter than input transfer conduit 6 or compression chamber 1. This lower diameter acts to develop a back pressure within the system thereby causing output valve 4 to remain closed for a longer period. More particularly, Bernoulli principles are employed to interrupt the fluid flow at the point where the flow channel diameter decreases in size. While the velocity of fluid increases at this point, a back pressure is created which maintains spring loaded output check valve 4 in the closed position longer than would normally be experienced in a conventional hydraulic pump assembly. This function thus extends the pressure application period within compression chamber 1 which in turn facilitates physical modification to substrate 40 and its properties.

Figure 2B:
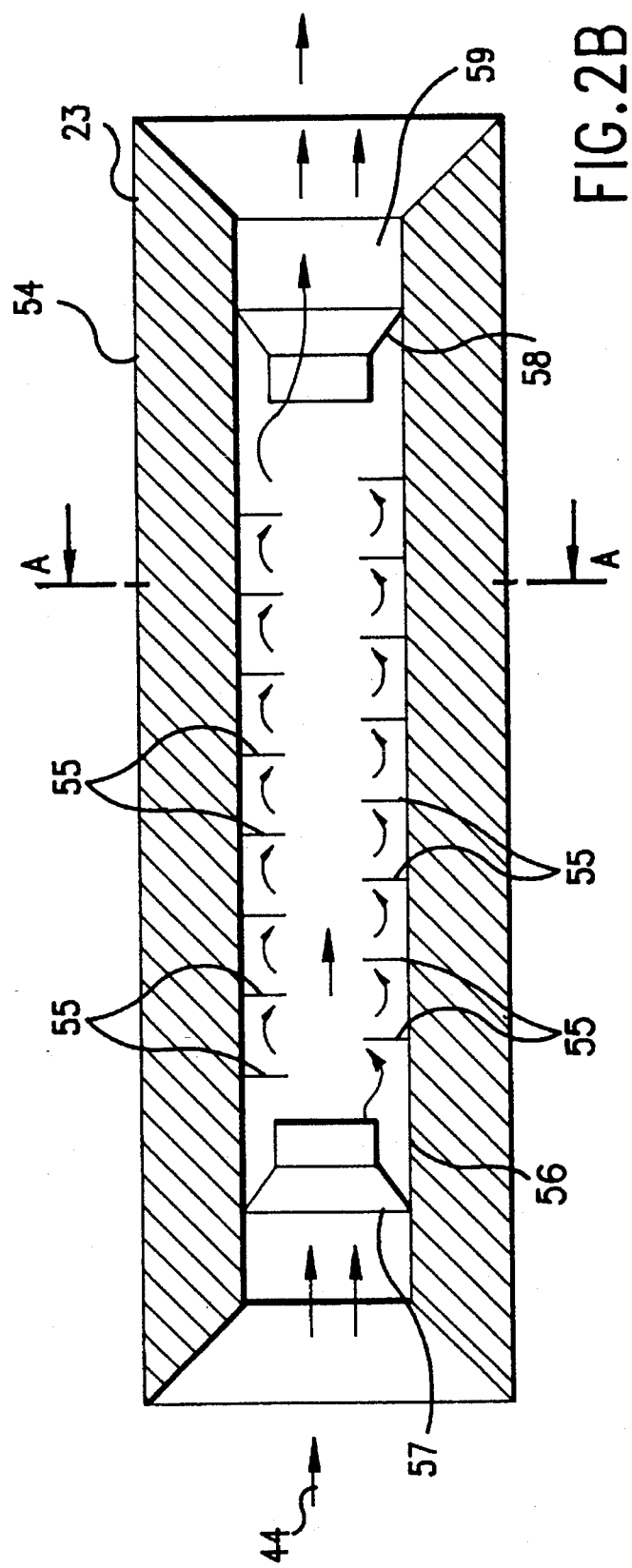
FIG. 2B is a cross section of the baffled chamber of FIG. 2A taken along axis A—A.

Secondly, baffled chamber 23 (FIG. 2A) comprises a housing 54 within which a plurality of tabs or baffles 55 are provided for the purpose of inducing turbulence within the fluid and further adding to the back pressure effect discussed above. The length of chamber 23 may be varied to increase or decrease turbulence and back pressure to effect various physical property changes. Pressure treated substrate 40 enters the chamber 23 through inflow nozzle 57 which is contained within the inner diameter 56 of housing 54. Baffles 55 are actually a series of rings in the preferred embodiment as shown in the cross section (FIG. 2B). Baffles 55 protrude from the ring into the fluid flow causing turbulence and shear within the pressure treated substrate 40. It is theorized that the turbulence further promotes cavitation; an effect which will be discussed in greater detail below. It should be noted that other suitable means may also be employed to regulate the timing of valves 3 and 4 with departing from the intended purpose.

Compressed air 30 is delivered through an air conduit channel 8, an air filter 9, a regulator 10, an air flow oiler reservoir 12, a ¼ turn air valve 14, and into an air motor 22. Air filter 9 is used to drain water from the compressed air supply 30. Regulator 10 controls the air pressure measured by pressure gauge 11. Minute oil droplets are introduced in the compressed air supply 30 as the air flows over a oil reservoir 12 to lubricate the air motor 22. Air motor 22 exhausts spent air through a muffler 15 which is connected to the outflow air port 17 of the air motor 22.

Air motor 22 cycles forward and backward as a result of the compressed air flow. The number of strokes of piston 20 (FIG. 1B) is controlled by ¼ turn air valve 14. A 90 degree incremental dial 13 is placed on valve 14. At setting zero, the valve is fully closed and no air flows to the air motor 22. At setting nine, which is 90 degrees to the horizontal, the valve is fully open and the full volume and force of the compressed air 30 is delivered to air motor 22. The ¼ turn air valve 14 is therefore the speed regulator of pressure applicator system 2, generally, and the stroke regulator of piston 20, specifically.

OPERATION

The substrate 40 is charged to reservoir 5 in any state capable of flow through the system such as a pure liquid or carried by another liquid in the form of a mixture, solution, dispersion, suspension, emulsion, slurry or otherwise. Substrate 40 may be processed in heated, cooled or ambient temperature depending on its flow properties. While a wide variety of substrates 40 may be employed either alone or in combination with the method and apparatus of this invention, for purposes of disclosure it is convenient to consider and demonstrate them by their application to a natural polymer: starch.

Figure 1A:
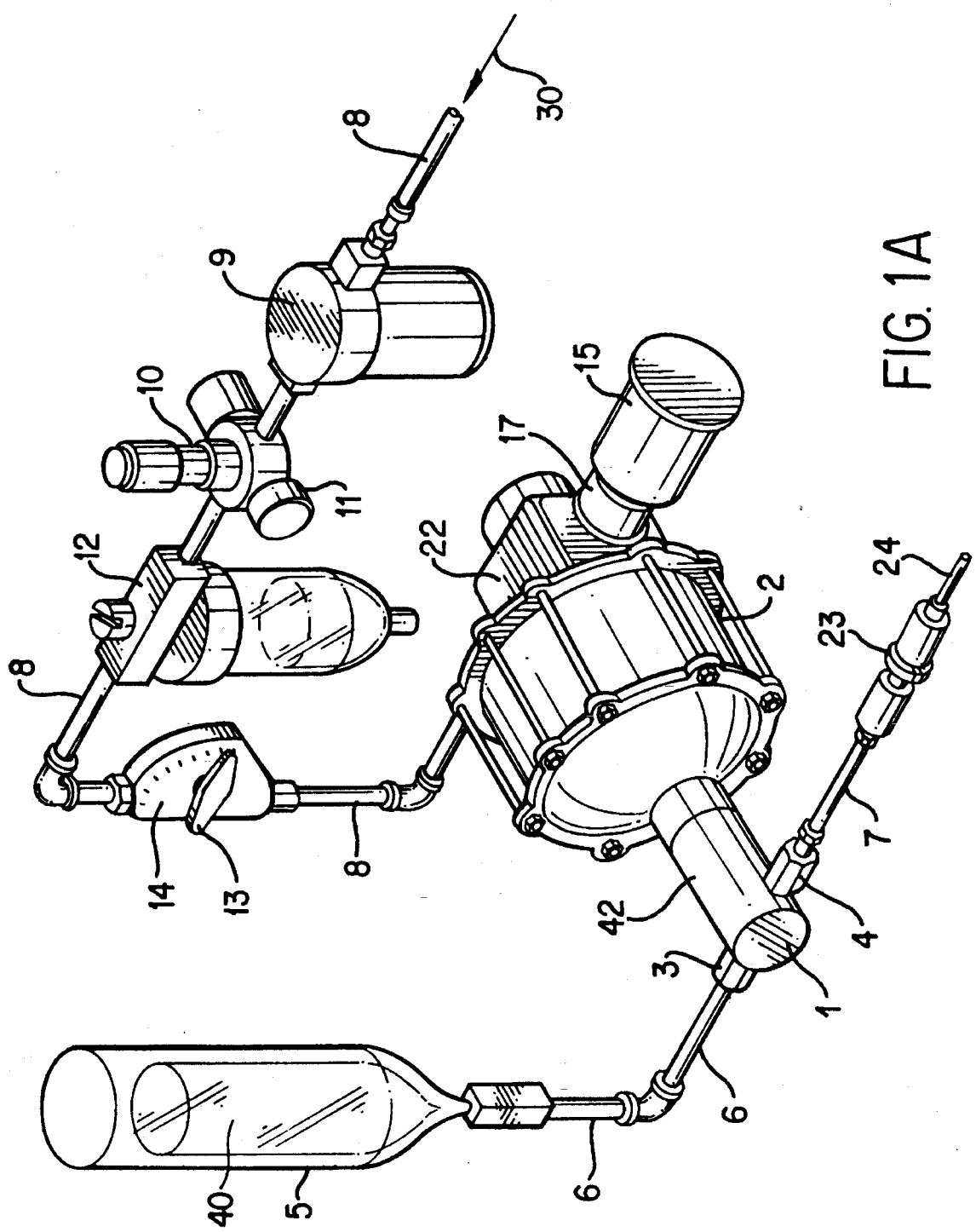
FIG. 1A is a Schematic diagram of the apparatus used to effect the modification of starch through abrupt pressure change treatments.
Figure 1B:
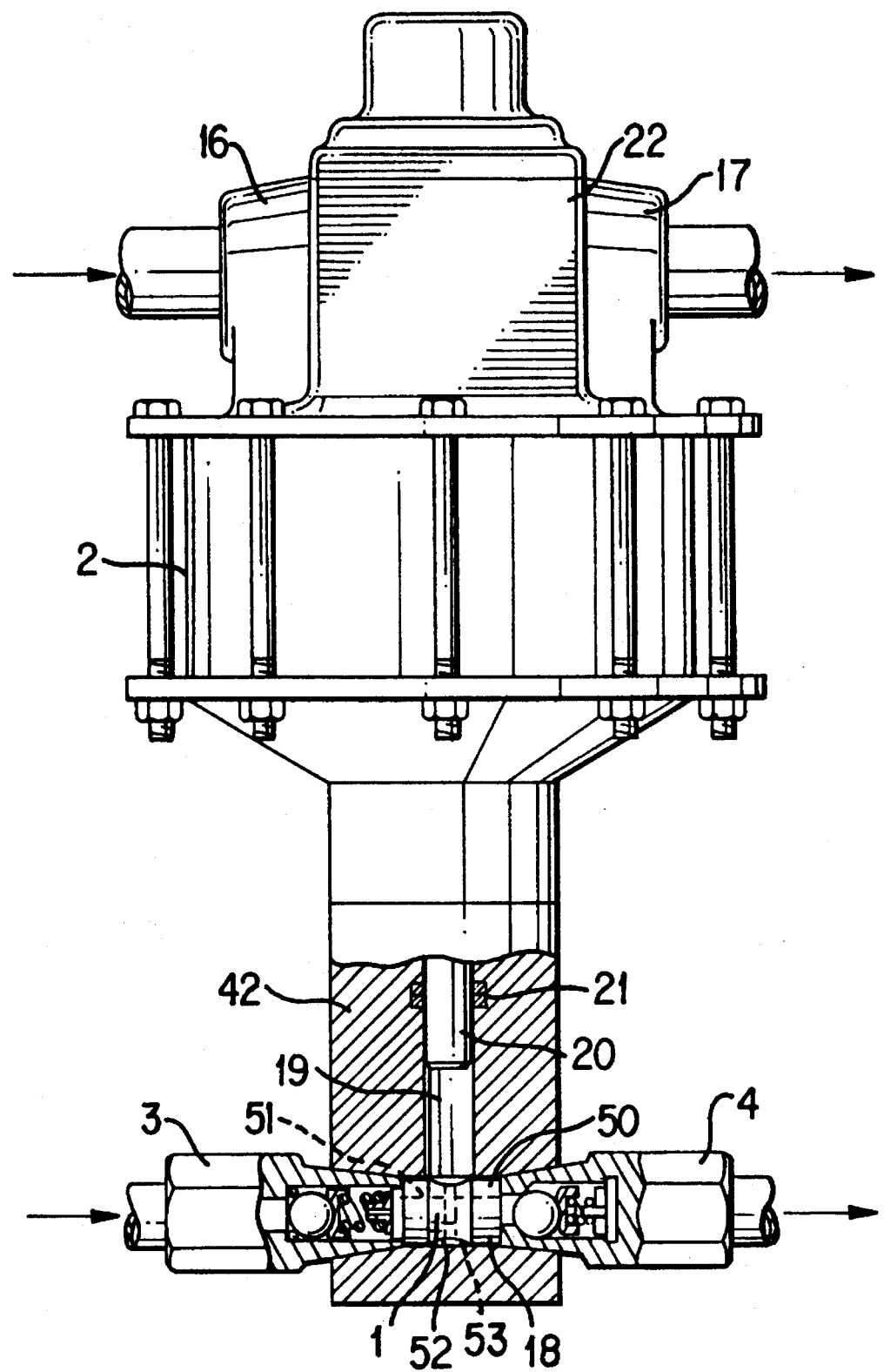
FIG. 1B is a schematic diagram of the piston component of the pressure treatment apparatus used to effect the modification of starch through pressure shock treatments.

Starch 40 is passed through the apparatus of FIGS. 1A and 1B and is pressure treated as the piston 20 strikes downward on its positive and negative displacement cycle within the pressure applicator housing 2. Valves 3 and 4 may be locked in the closed position while piston 20 is applying pressure to the starch 40 trapped between the valves in the compression chamber 1. Alternatively the valve action may be adjusted to provide a semi-continuous flow process. As piston 20 is raised through its negative pressure cycle within nose housing 42, a quantity of starch 40 is drawn past inlet valve 3 and into compression chamber 1 where it is trapped when outlet valve 4 is in the closed position. As piston 20 is forced downward by air motor 22, it begins its pressure application or downward positive stroke cycle while both valves 3 and 4 remain closed for a period of time sufficient to produce the desired pressure intensity within compression chamber 1. Spring loaded outlet valve 4 is adjusted to open when the desired pressure is reached permitting the treated starch 40 flow from the compression chamber 1 through outlet transfer conduit 7 which may be heated and/or reduced in diameter for purposes described above. Baffle chamber 23 may similarly be employed, with or without the reduced diameter of conduit 7, to impart increased turbulence and back-pressure effects as earlier described. Substrate 40 finally exits the system through exit conduit 24 for delivery into a collection vessel (not shown) for storage or subsequent drying. Alternatively, starch 40 may be recycled through the apparatus for exposure to additional pressure treatments or may be directed to one or more similar systems connected in series or parallel.

The resulting starch end-product manifests several changes in physical properties, including: an altered thermal profile (the onset of melting and the actual melting point is raised, the heat energy required to effect melting is also altered); altered disintegration and solubility properties (the solubility rate in water and other solutions in an ambient or heated environment is slowed by as much as 300%); an altered viscosity profile (pressure treated starch exhibits a higher viscosity for a longer period of time); an altered tableting profile (the treatment of waxy maize pre-gelatinized starches results in a starch which forms harder tablets at lower than conventional compression forces); and an altered turbidity profile (the clarity of solutions made with pressure treated starch is improved).

A feature of the subject apparatus believed to aid in these modifications of starch and its physical properties can be found within piston assembly 2. Reference is once again made to FIG. 1B wherein one or more inserts or baffles 52 and 53 are placed within compression chamber 1 to retard fluid flow. These baffles 52 and 53 act to create turbulence within the compression chamber during pressure treatment and as starch 40 is pumped through piston assembly 2. Applicant theorizes that these baffles further act to generate cavitation within the compression chamber 1 as the piston 20 generates a abrupt pressure change.

The abrupt pressure change is believed to cause the liberation of gases trapped within the starch substrate 40, thereby generating heat. Various studies on cavitation show that the heat produced immediately upon cavitation can be very intense (5,000 degrees K or greater), even if only for a short period of time. The heat energy released is thought to be a major cause in the alteration of the physical properties of starch and other substrate compositions. Reference is made to the article, "The Temperature of Cavitation", by Flint and Suslick, American Association for the Advancement of Science, Sep. 20, 1991, Volume 253, pp. 1397–1398, wherein the heat energy caused by ordinary cavitation is discussed. Applicant theorizes that the heat energy released through cavitation is sufficient to cause a thermoreaction in the target substrate thereby contributing to its modification and that of its physical properties.

Moreover, applicant theorizes that the amylose and amylopectin components of the starch substrate 40 can be merged, compressed or deformed by the kinetic, compression and/or shear forces resulting from the abrupt pressure changes generated within the compression chamber 1. Applicant, however, does not rule out as a possible mechanism the alternative possibility that it is the release of pressure forces, either during the pistons negative displacement or by the release of the pressurized starch through the check valve which contributes to property modification. It is possible that the chemical structure may be changed. Some substrates could be converted from an ionic to an anionic charge. Applicant has discovered the effect but does not know the mechanism.

A series of experiments were conducted to illustrate the effect of pressure treatments upon starch. In each case a device known as the Delta Processor, Model Number D-001 was employed. The device corresponded to the design illustrated in FIGS. 1A and 1B. The pressure applicator employed was a modified hydraulic pump supplied by S.C. Hydraulics Company, Model Number 10-600-8-ss-si. The tension on the output check valve was adjusted to open far slowly than would normally be the case for this model hydraulic pump. A calibration was made of the machines capabilities using distilled water to test the flow rate of the modified pump assemblage and the number of strokes per minute.

The apparatus employed in all of the following experiments was set at speed dial 4 and at either 60- or 90 psi on the regulator gauge. The pump system, however, multiplies the effective force of compression by 144×. The pressure applied in the compression chamber is effectively 8,640 lbs. at the 60 psi regulator position. At the 90 psi regulator position, the effective pressure in the compression chamber is 12,960 lbs.

The timing of the opening of the output check valve controls how long the piston is in a downward or positive pressure position, i.e. how long the target substrate is under pressure. In the experiments described below, the machine was set for speed dial setting 4 at either 60 or 90 psi. At the 60 psi setting, speed level 4, the transition time, the time by which the substrate was under direct positive compression was measured at 0.59 seconds. At the 90 psi setting, speed level 4, the transition time was measured at 0.53 seconds. The difference between the two pressure settings alters the transition time by only 0.06 seconds, but the effective pressure differential was 4,320 psi.

EXPERIMENT 1

300 grams of Capsul starch provided by National Starch Co., Inc. is mixed in 700 Mls distilled water at ambient temperature in a one liter beaker and stirred for 15 minutes until the Capsul starch is dissolved. The solution is then fed to the Delta Processor Unit Model No D-001, supplied by Encapsulation Systems Inc. The unit is set for either 60 or 90 psi inlet pressure and the samples treated by a single pass through the apparatus. The effective pressure is multiplied 144 times to produce either 8,640 lbs. or 12,960 lbs. of pressure respectively. The treated starch is then delivered to a commercial spray drier device and dried to produce a dry powder product with less than 6% moisture.

Figure 3A:
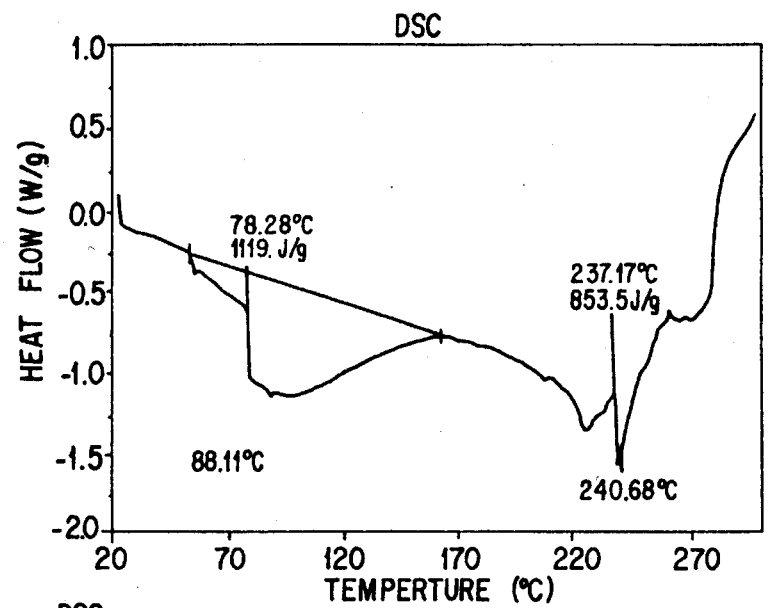
FIGS. 3A through 3C compare various DSC spectra of a starch known as Capsul. Sample 1 is the DSC spectra this particular starch as it is supplied by the manufacturer in a raw untreated state. Sample 2 is a DSC spectra of Capsule starch after it has been treated by pressure at setting 60 for 5 recycle passes through the pressure treatment apparatus depicted in FIG. 1. Sample 3 is a DSC spectra of Capsule starch after it has been treated by pressure at setting 90 for 5 recycle passes through the pressure treatment apparatus depicted in FIG. 1.
Figure 3B:
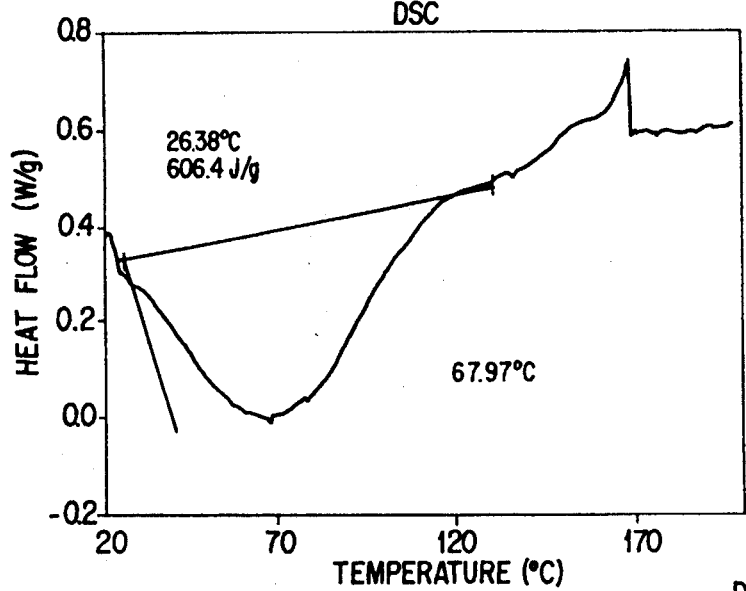
Figure 3C:
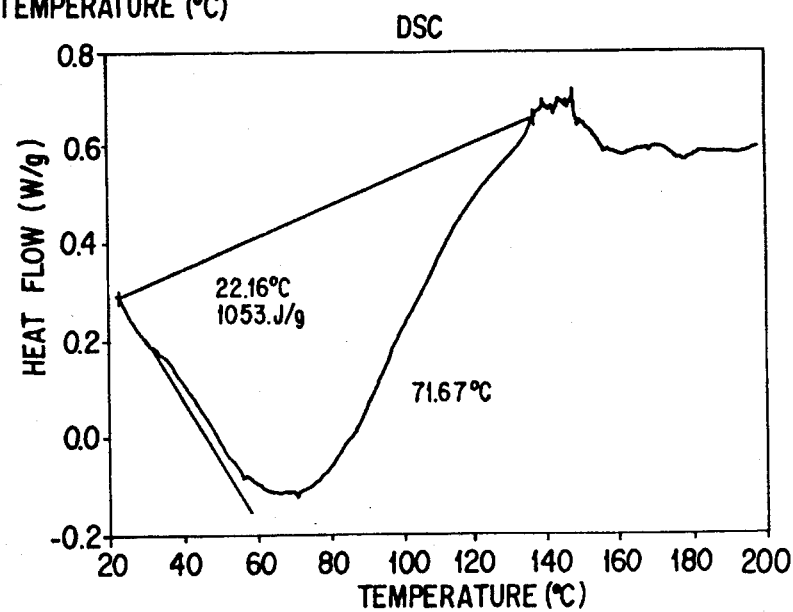

FIGS. 3A–C depict DSC spectra of the resulting starch products. A differential scanning calorimeter device supplied by Dupont Instruments Corp. Model Number TA-2000 was employed.

Two comments are in order with respect to the DSC spectra presented below. First, the absolute height (or depth) of the peaks in the DSC spectra are reflective only of the mass of the sample used to generate that curve. Thus, differences in the height (or depth) of a peak from one spectra to another are not significant in terms of identifying potential changes in polymorphic structure or in the amylose to amylopectin ratio. The different polymorphic forms are distinguished by the fact that they melt at different temperatures. Secondly, all the DSC spectra have been presented at the same resolution and scale unless otherwise specifically noted.

The use of DSC spectra to characterize the physical structure changes in the target substrate was chosen to determine if any significant alterations in thermal profile or crystallinity structure had occurred as a result of this process. In many cases, the DSC spectra reveal a major shift in the thermal character of the substrate after treatment. This was clearly most evident on those compositions which exhibit a polymorphic crystalline structure such as starch.

FIGS. 3 are the DSC spectra of raw Capsul starch compared to Capsul starch pressure treated at both 90 and 60 psi. Graph 3A depicts the DSC spectra of raw Capsul Starch. Graph 3B shows Capsul starch which has been treated at the 60 psi setting. Graph 3C shows Capsul starch which has been pressure treated at the 90 psi setting. The significant difference relates to the starting point of melting of the starch products. The onset of melting begins at 78.28 (c) for the raw capsule starch. After pressure treating at the 60 psi setting for one pass the onset of melting is lowered to just 26.38 (c). After pressure treating at the 90 psi setting for one pass the onset of melting is lowered even further to 22.16 (c).

These DSC profiles clearly show that the thermal profile of starch may be altered through pressure processing.

EXPERIMENT 2

300 grams of Capsul starch is mixed in 700 Mls distilled water at ambient temperature in a one liter beaker and stirred for 15 minutes until the capsul starch is dissolved. The solution is then fed to the Delta Processor Unit Model No D-001, supplied by Encapsulation Systems Inc. The unit is set for 90 psi inlet feed pressure. The effective pressure is multiplied 144 times to produce 12,960 lbs. of pressure upon the treated sample. The starch solution was subjected to either one pass through the process or twenty passes and compared with an untreated control solution.

The end-product was collected and, instead of spray drying, the solution was placed into a vacuum oven and dried at just 50 (C) under a vacuum until dried. The resulting product at this stage was crystalline in appearance and in the form of large agglomerates. These dried crystals were then ground in a ball mill grinder until a dry powder was obtained, a final product with less than 2% moisture. This resultant product was then tested through a series of procedures to determine if it had characteristics different from the raw starch.

Figure 4A:
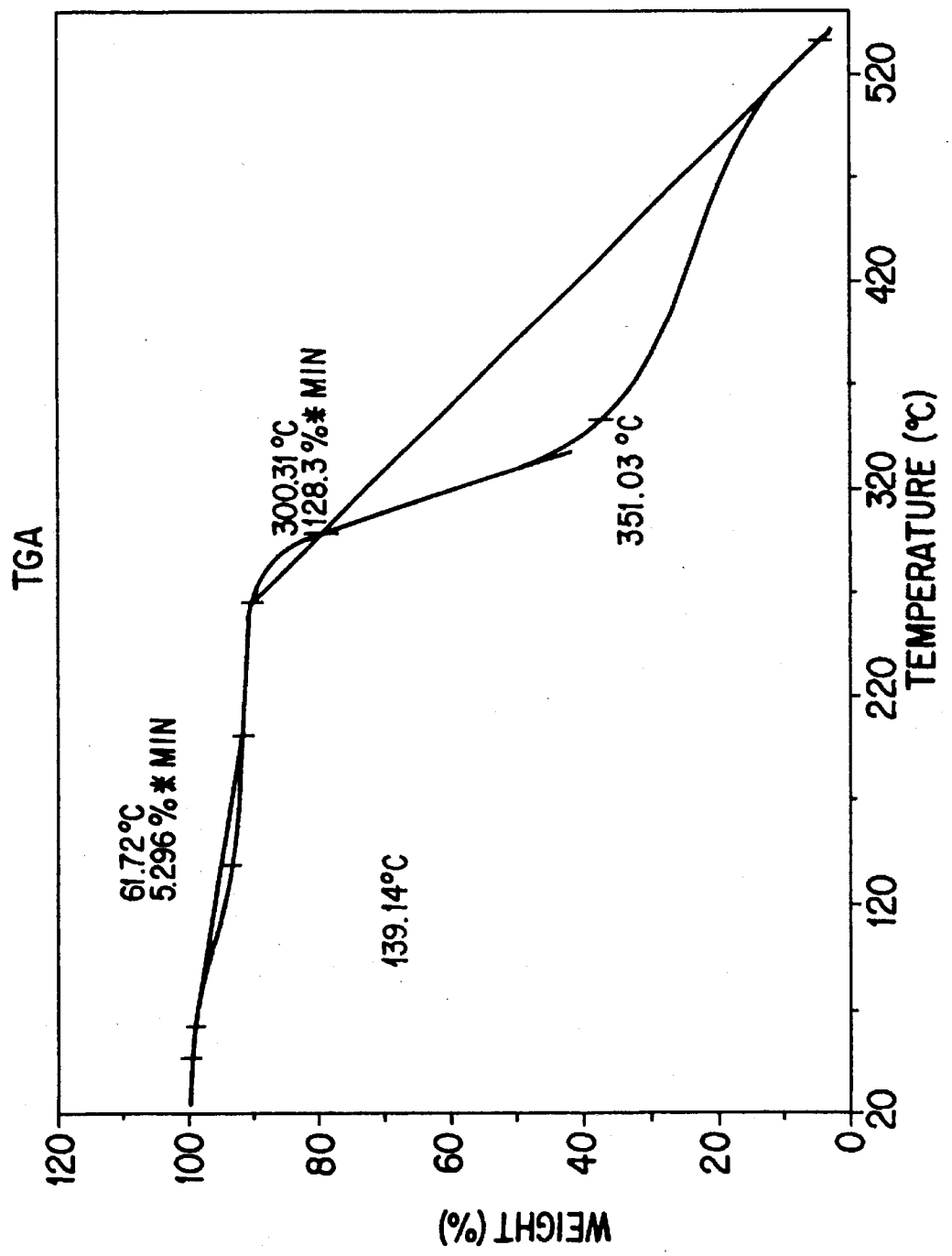
FIG. 4A Shows the TGA spectra of Capsul starch which has been dissolved into a solution and then dried in a vacuum oven into a dry powder.
Figure 4B:
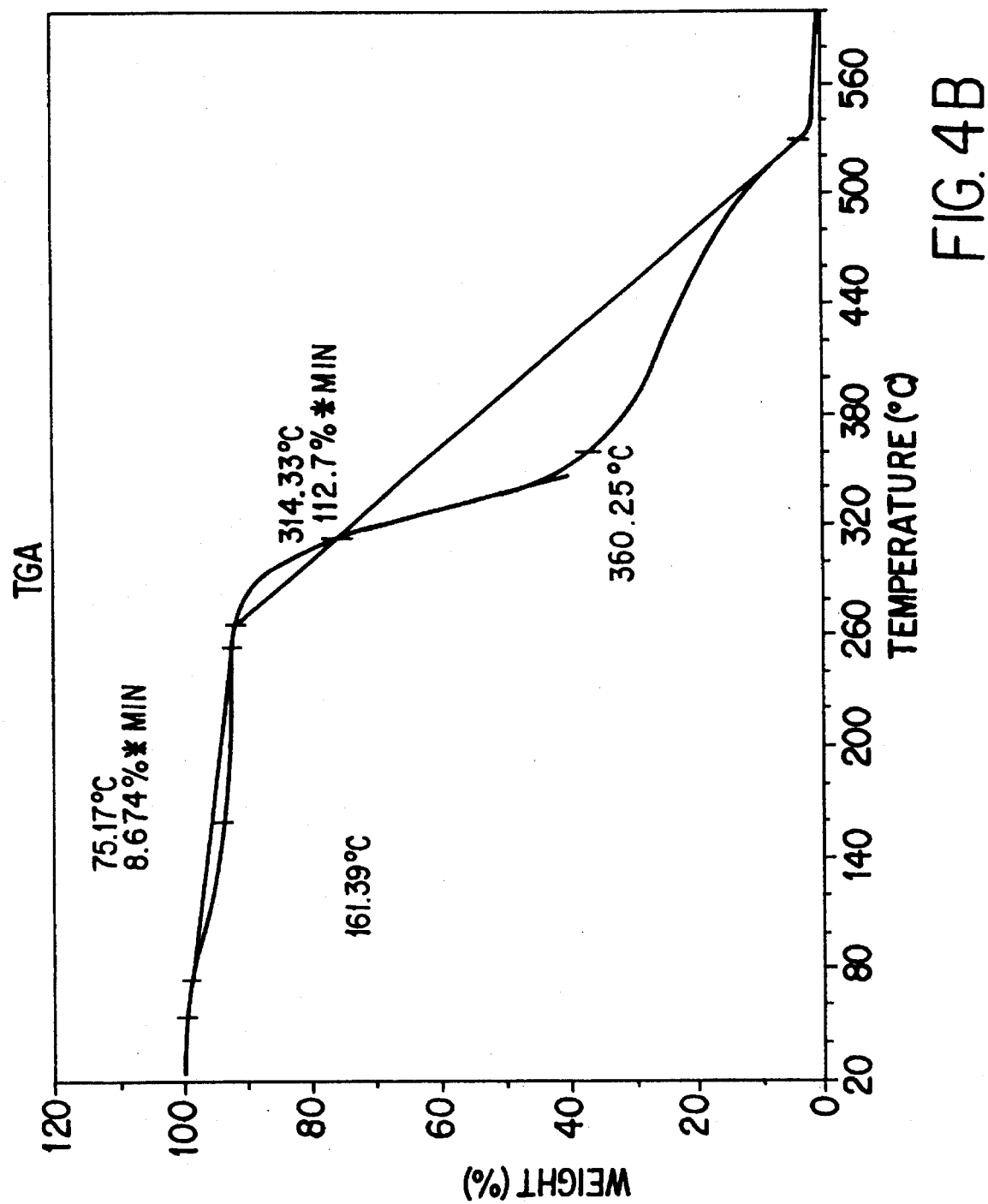
FIG. 4B shows the TGA spectra of Capsul starch which has been dissolved into a solution, pressure treated by the apparatus depicted in FIG. 1 at setting 90 at just one treatment pass through the apparatus and then vacuum dried into a dry powder.

FIGS. 4A–C show the results of thermographic analysis of the Capsul starch which has been treated by the methods described in Experiment 2, with no pressure processing, as compared to two samples which were pressure treated. FIG. 4A is the recovered control sample, with no pressure treatment. Note the start of thermal degradation begins at 61.72 (c). After one pass (FIG. 4B) through the pressurization process the start of degradation jumps to 75.17 (C); a gain of 13.45 degrees. When treated for 20 passes (FIG. 4C) the onset of degradation begins at 67.10 (C), still a gain over the control sample but far less than was achieved through the single pass sample. All of the pressurization samples were treated at the 90 psi setting.

Again the thermal profile is altered after pressure treatment. In the above example it can be seen that multiple pressure treatments can vary the thermal profile of a pressure treated starch, and that there are significant gains in thermal stability properties provided through pressure treatments.

EXPERIMENT 3

100 lbs of Hylon 7 starch is mixed in 25 gallons distilled water at ambient temperature in a 50 gallon stainless steel tank and stirred for 30 minutes until the starch is dispersed. Hylon 7 is the name of high amylose starch supplied by National starch. It contains 70% amylose and is often used as a gelling agent for jelly gum candies. Hylon 7 does not dissolve readily in water at room temperature.

The dispersion is then fed to the Delta Processor Unit Model No. D-001, supplied by Encapsulation Systems Inc. The unit is set for either 60 or 90 psi inlet feed pressure.

The end product is then delivered to a tank where the excess water is eventually siphoned off, producing a wet cake product. The wet cake is then placed in a vacuum oven which is heated to 40° (C.) to draw off the remaining moisture. A final dry product containing less than 5% moisture is produced which was then tested through a series of procedures to determine if it had characteristics distinguishable from the raw starch.

Figure 5A:
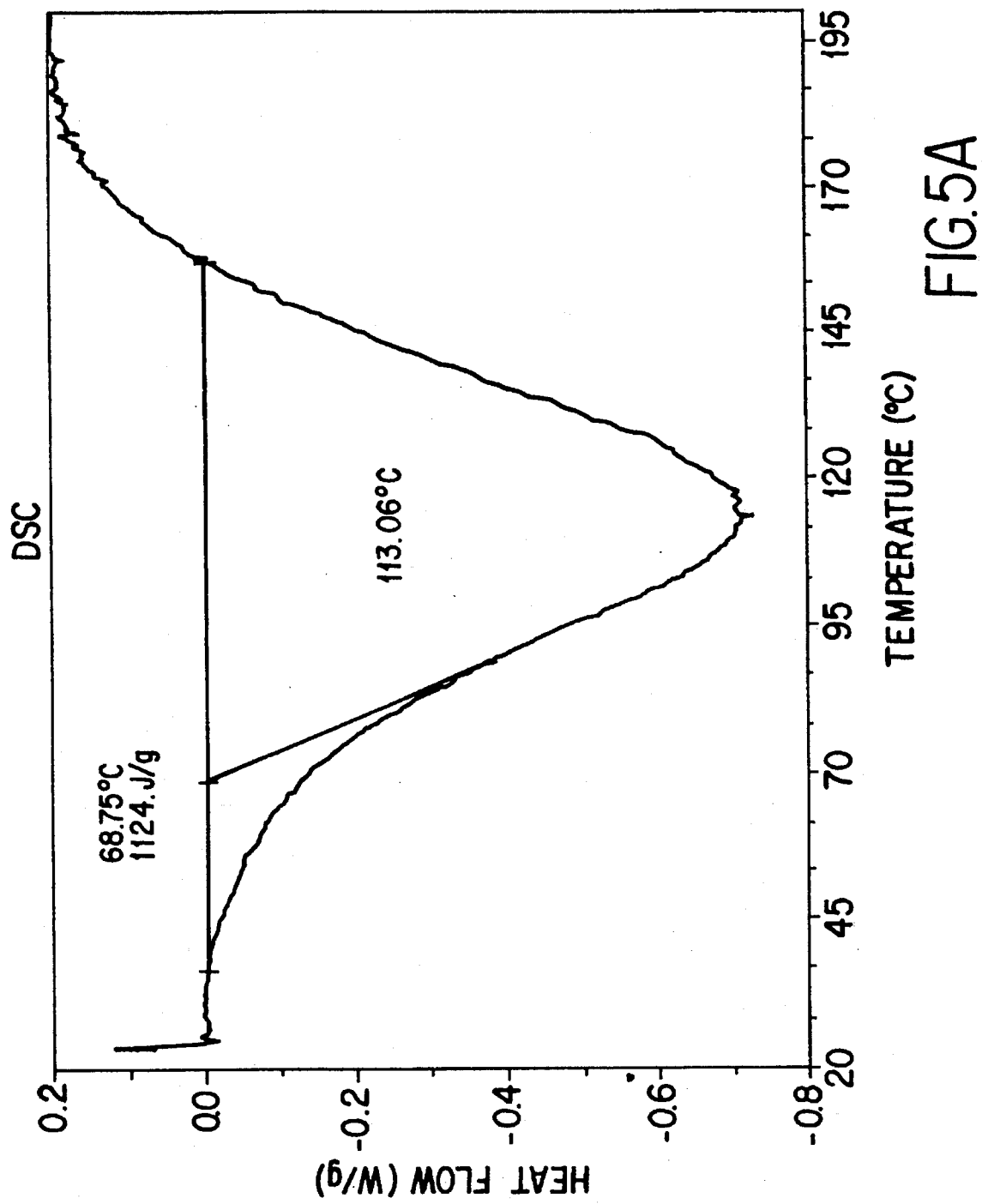
FIG. 5A is a DSC spectra of a starch known as Hylon 7 as supplied from the manufacturer, National Starch Co., in a raw untreated state.

FIG. 5A is the DSC spectra of Hylon 7 starch, supplied by National Starch Co., in raw form.

Figure 5B:
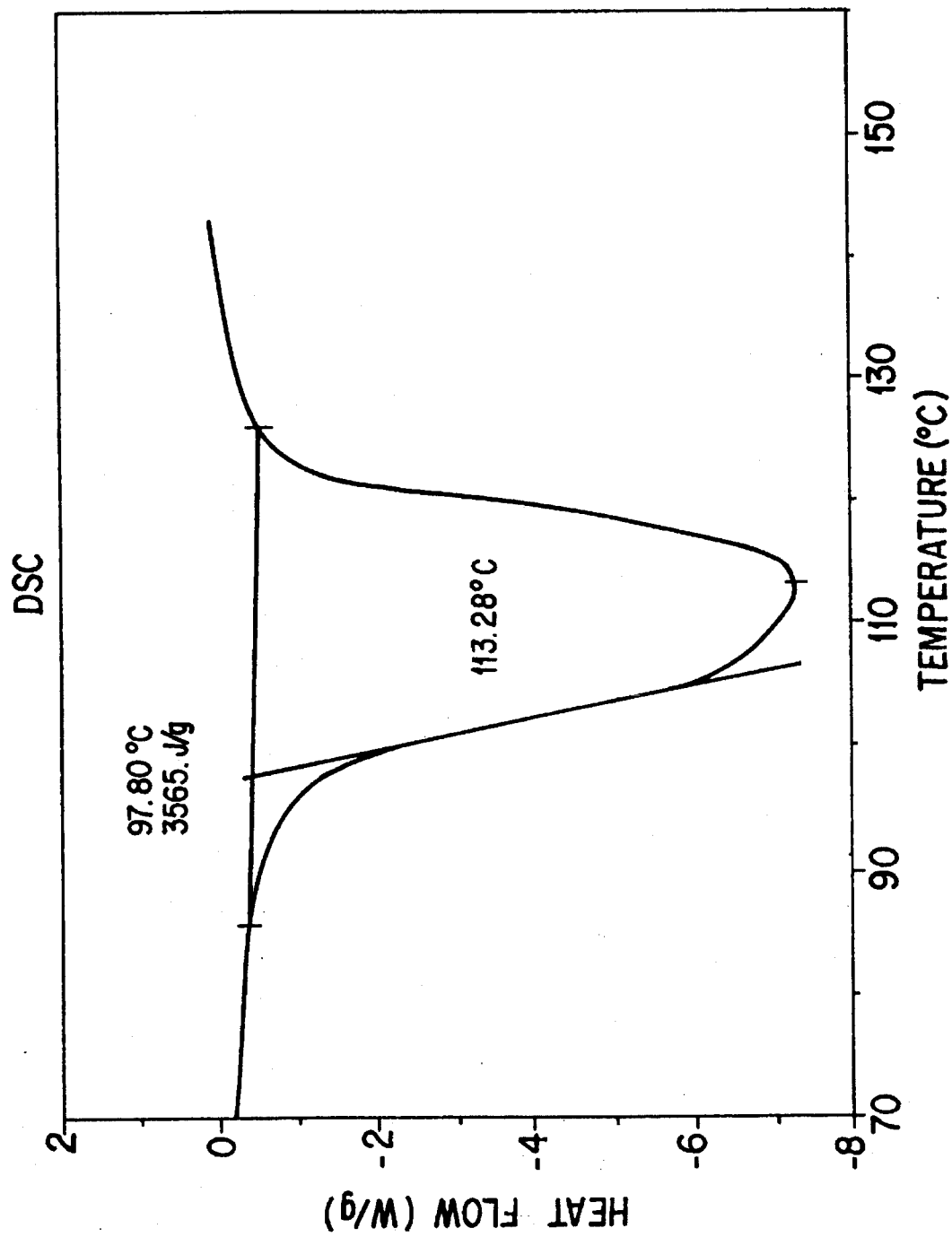
FIG. 5B is a DSC spectra of Hylon 7 starch after it has been treated by pressure in the device illustrated in FIG. 1 at setting 90 for one pass.

FIG. 5B is the DSC spectra of Hylon 7 starch which has been pressure treated at the 90 psi setting. Note the extreme gain in the onset of melting between the two samples. The raw sample begins to melt at 68.75° (C.) while the pressure treated sample does not begin to melt until 97.80° (C.); a gain of 29.05 degrees. The melting in both samples is completed at nearly the same point, 113° (C.), but more thermal energy is required to begin the melting of the pressure treated sample.

Figure 6A:
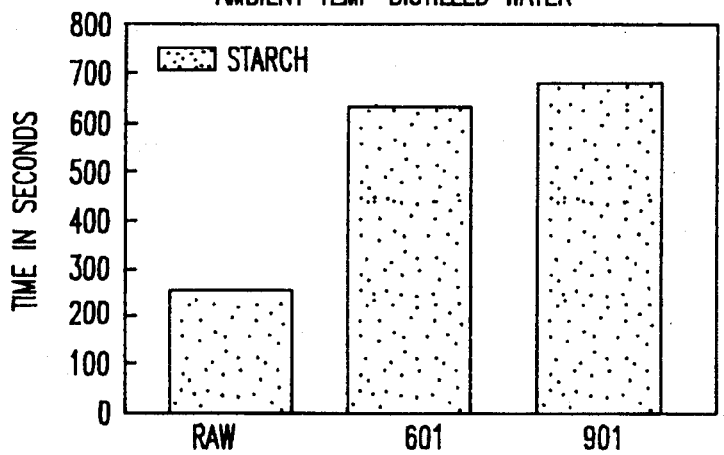
FIG. 6A is a solubility rate comparison of raw Capsul starch compared to two different forms of pressure treated starch, in ambient water.
Figure 6B:
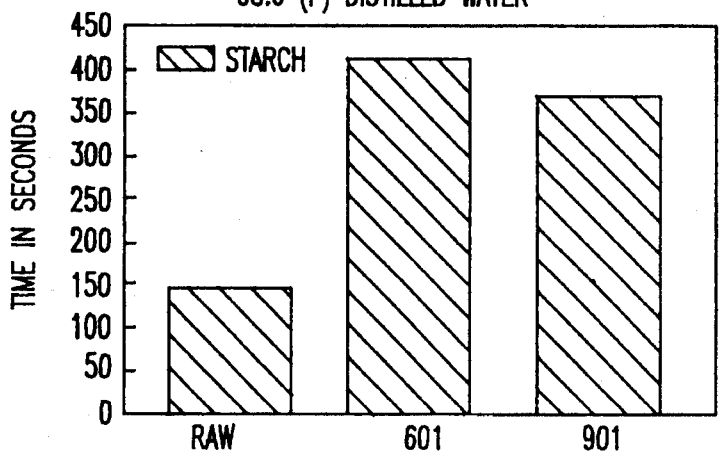
FIG. 6B is a solubility rate comparison of raw Capsul starch compared to two different forms of pressure treated starch, in heated water.
Figure 6C:
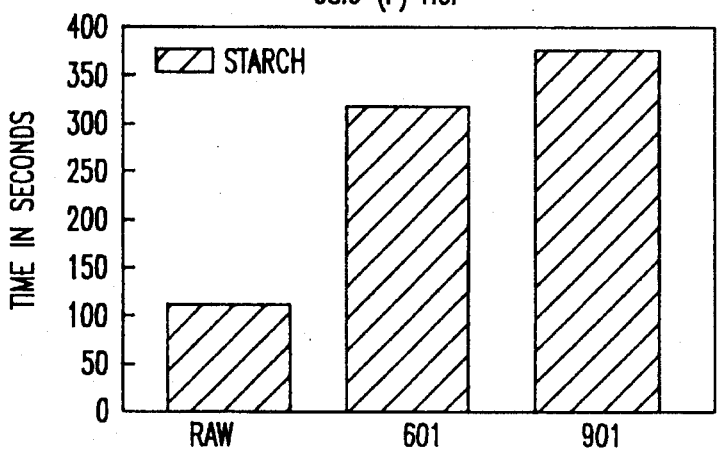
FIG. 6C is a solubility rate comparison of raw Capsul starch compared to two different forms of pressure treated starch, in a warmed solution consisting of 1N HCl and water, simulating human gastrointestinal fluids.

FIGS. 6A–C illustrate the dissolution profile for starch materials made according to the procedure described in experiment 1, whereby FIG. 6A is a dissolution profile for raw Capsul starch vs. pressure treated starches processed at the 60 psi and 90 psi settings, in ambient water. FIG. 6B depicts the same tests but in heated water and FIG. 6C depicts the results of the same tests in a 1N HCl solution, simulating human gastric fluid conditions. In each test, one gram of substrate was dissolved in 50 ml of the given solvent in a 150 ml flask subjected to a low setting shaker bath. Dissolution is the point at which the starch totally dissolves and the flask is clear according to either a visual observation or through the use of an ultraviolet spectrophotometer.

The time for complete dissolution is given along the "Y" axis in seconds. The "601" designation denotes that the sample was pressure treated at the 60 psi setting for 1 pass. Similarly, the "901" designation denotes a 90 psi pressure setting for 1 pass.

The graphs of FIGS. 6A–C represent an average of 5 readings for each sample in each tested media and temperature condition. In each case the pressure treated capsule starch dissolves far slower than the untreated raw starch. There were unexpected differences between the 601 and 901 products in differing media. For example, the 601 product has a slower dissolution in warm water than does the 901 product. Generally, however, the 901 product has a slower dissolution time in most media tested.

Figure 7:
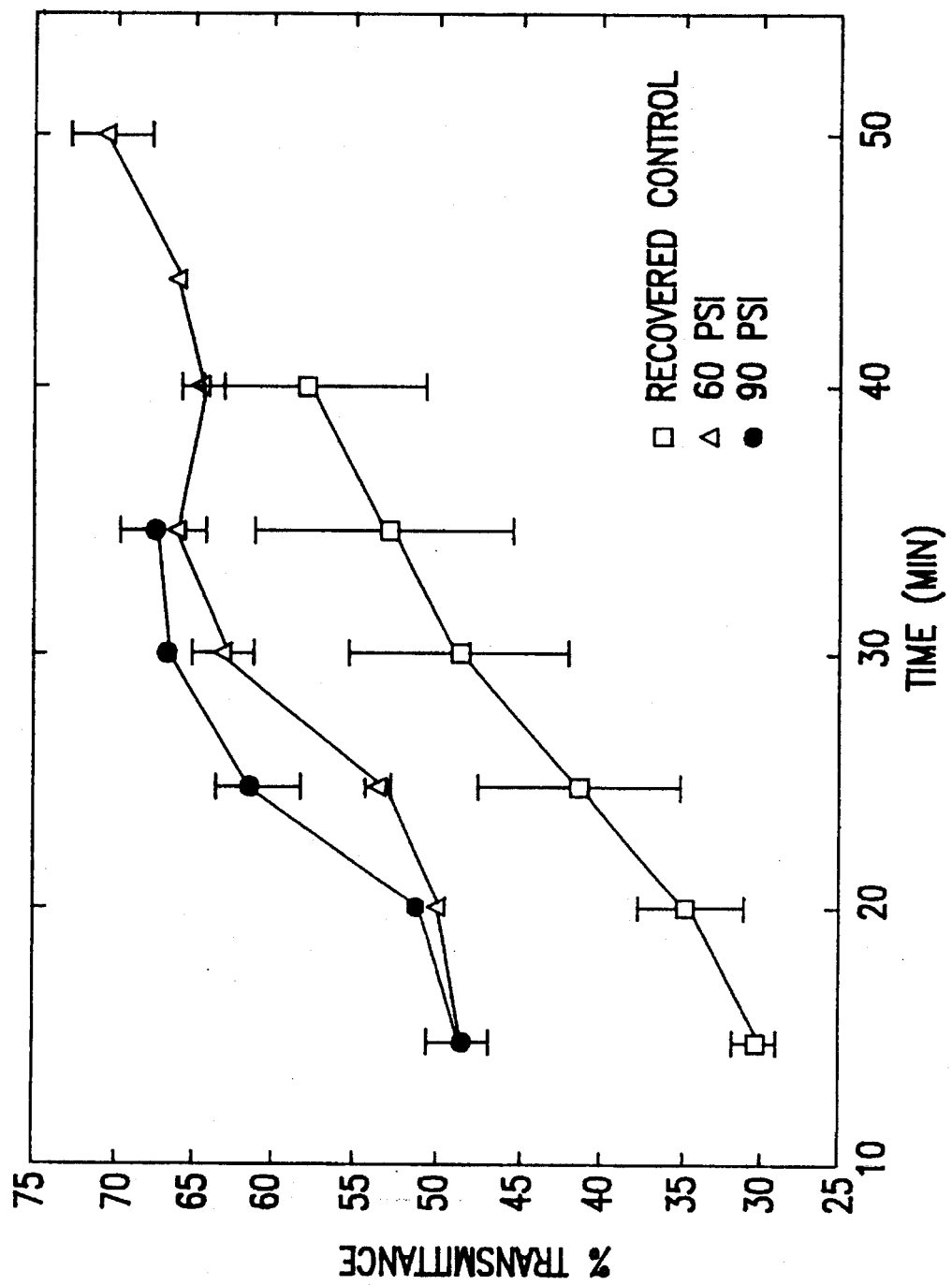
FIG. 7 is a turbidity profile of raw capsule starch vs. two different forms of pressure treated Capsul starch.
Figure 8A:
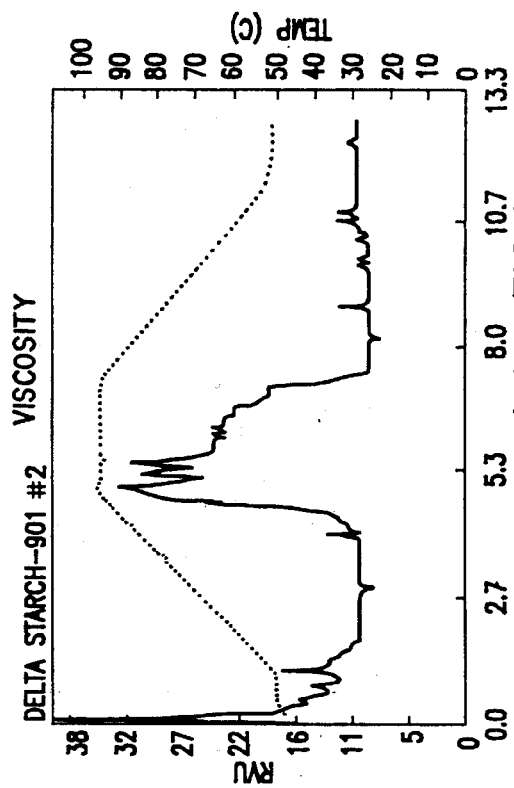
FIGS. 8A through 8O are viscosity profiles indicating a comparison between raw capsul starch and pressure treated capsul starch.
Figure 8C:
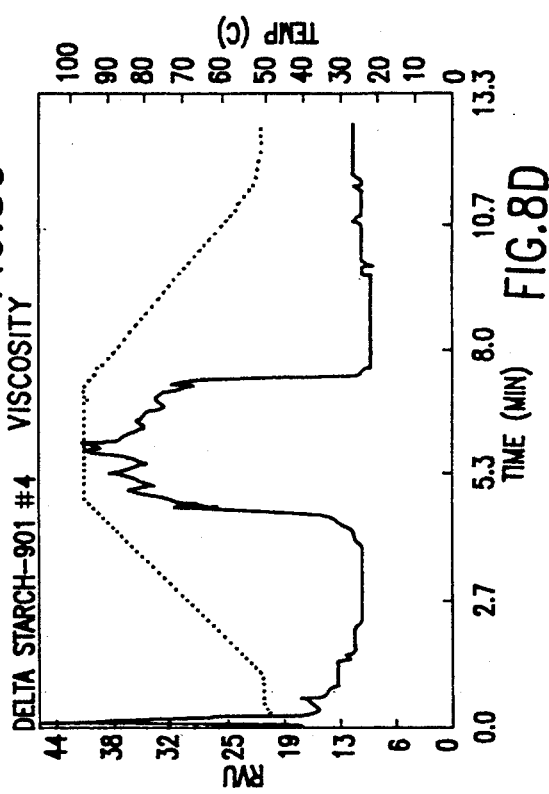
Figure 8B:
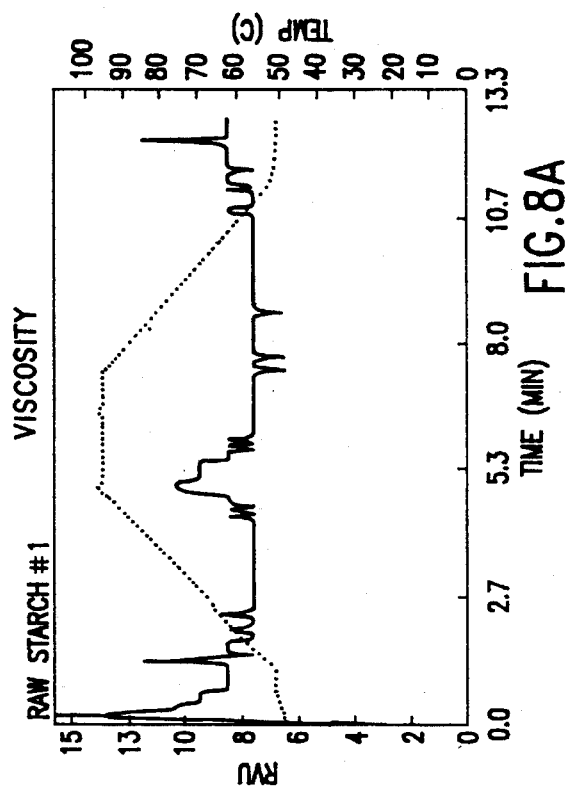
Figure 8D:
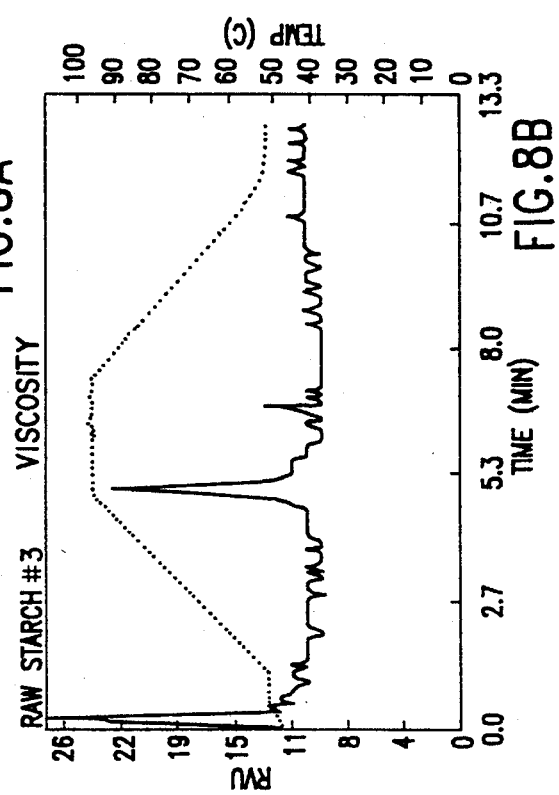

The graph depicted in FIG. 7 shows the effect of pressure treatments on turbidity of the Capsul raw starch vs. the pressure treated samples made in experiment 1. Turbidity is the measure of transmitted light through a fluid. It is used to determine the cloudiness of liquids. The graph of FIG. 7 shows a comparison of turbidity for the raw starch compared to the pressure treated starches, treated at setting 60 psi and 90 psi.

A series of 1% solutions of the starch in distilled water were prepared and tested for their UV spectra using a Perkin-Elmer Lambda 38 UV spectrophotometer. A reading was taken at various time intervals of the percent light penetration operating at 600 nm wavelengths of ultraviolet transmission. From the graph it can be seen that the greatest light penetration and hence, the clearest solution, is exhibited by the pressure treated starch samples, with the greatest clarity profile exhibited by the sample treated at 90 psi.

FIG. 8 provides a comparison of the relative viscosity profiles of raw Capsul starch and pressure treated starch processed at the 90 psi setting from Experiment 1. FIG. 8 reveals four plots representative of two different batch runs through a Rapid Visco-Analyzer, model no. RVA3D, from Foss Food Technologies Inc. Viscosity profiles often indicate pasting characteristics for the starch. RVU=Relative Viscosity Units. The samples are heated over time and the viscosity is automatically measured and plotted.

Raw starch #1 and Raw starch #3, are from two different batches of raw Capsul starch as supplied by the manufacturer, Delta Starch 901 (#2) and Delta starch 901 (#4) are two different samples of the pressure treated Capsul starch processed at 90 psi for one pass.

Examination of the graphs reveal that raw Capsul starch has a very short period during which it exhibits a high viscosity, and quickly looses that viscosity character over time. An examination of both raw starch visco-graphs indicates that there is poor uniformity within the raw starch batches.

The pressure treated samples, however, exhibit a greater uniformity between samples and also provide a higher viscosity profile for a longer period of time in comparison to the untreated samples. This result means that less heat energy is needed to achieve the desired viscosity profile; less heat, for a shorter period of time, passing on energy savings to the manufacturer. The use of emulsifiers and other thickeners may also be avoided through the use of the pressure treated starch products in certain food applications, because the pressure treated starch affords a superior viscosity profile.

Figure 9:
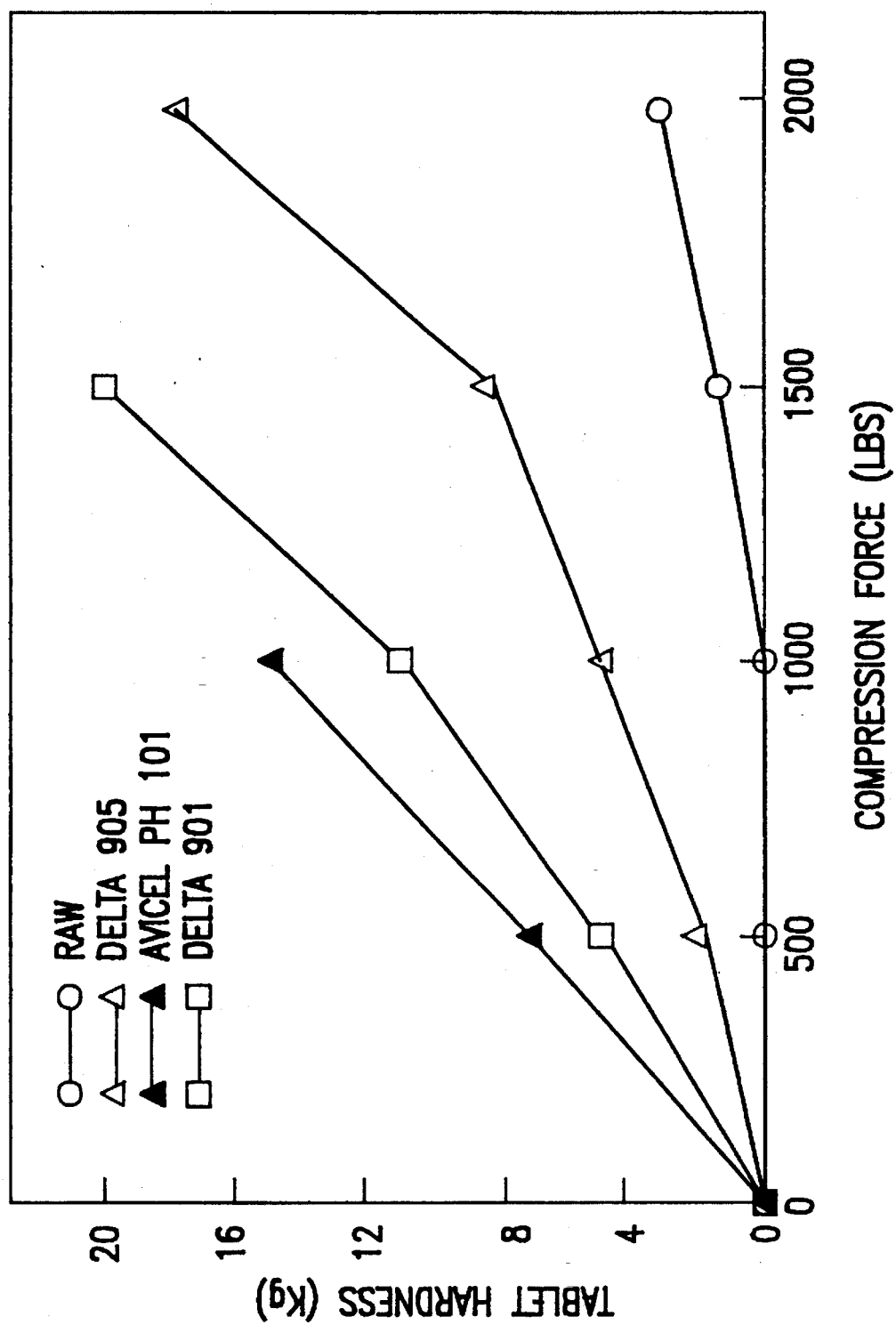
FIG. 9 is a Hardness profile of tablets made either Raw Capsul Starch, Pressure, treated Capsul Starch or Microcrystalline cellulose.

Treated starch samples were also tested as excipients in tableting processes to determine their respective hardness profiles. The need for a more readily dissolvable diluent than microcrystalline cellulose was identified in various pharmaceutical surveys of tableters. To test the effectiveness of pressure treated starch, initial tests were carried out by forming tablets composed of 100% starch vs. 100% microcrystalline cellulose. FIG. 9 reveals the hardness profile of the resulting pharmaceutical tablets.

Each tablet was composed solely of 200 mg. of the indicated material. No other binders or lubricants were employed. Raw Capsul starch was used as a base for comparison purposes along with Avicel Ph-101, a microcrystalline cellulose product supplied by FMC corporation. Standard tablets were made using a direct compression process in a Carver laboratory single stroke tablet press machine. The tablets were then tested using a conventional stokes tablet hardness tester device. The profile given in the graph of FIG. 9 reveals that the greatest hardness is exhibited by the pressure treated starch treated at 90 psi. Microcrystalline cellulose affords a high hardness and the pressure treated starch exhibits a high hardness as well but softer than the tablets made with either the 90 psi sample or the microcrystalline cellulose, while the raw starch affords a very soft tablet. In fact, the raw starch tablet was highly friable and broke readily in the hand.

The hardness profile reveals that the 90 psi sample provides the greatest hardness while requiring the lowest overall pressure treatment from the tableting press. Accordingly, starch treated at 90 psi may serve as an effective excipient for those active drug agents which are sensitive to the friction developed during tableting at high pressure tonnage and, therefore, difficult to tablet. The lower hardness profiles of the 60 psi end-products find utility as excipients in chewable tablet formations.

Figure 10:
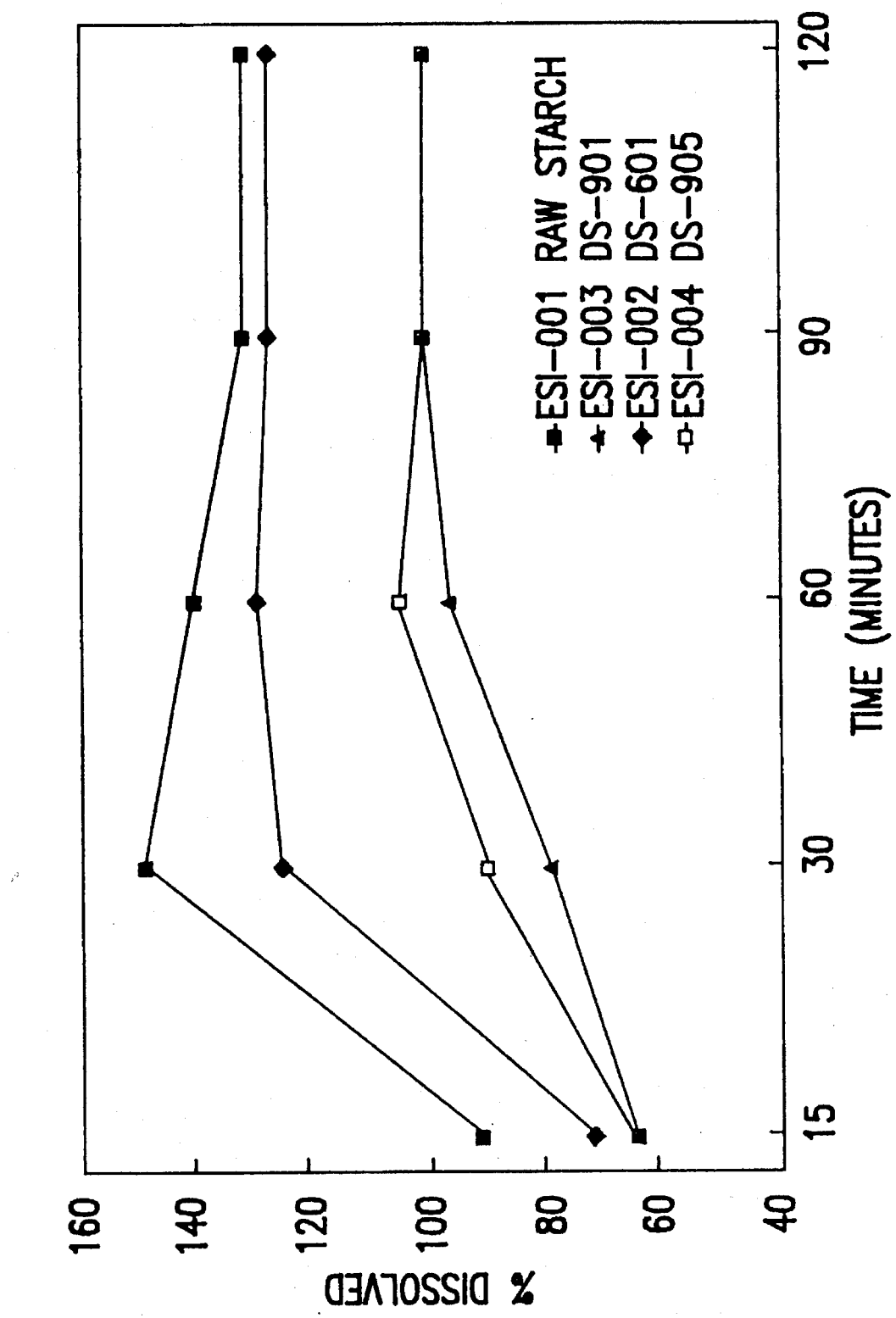
FIG. 10 is a dissolution profile of tablets made with 10% acetaminophen 90% starch, where the starch is either raw capsule starch or either of two pressure treated starch products.

Next, tablets were made using 10% acetaminophen and tested for a dissolution profile. FIG. 10 depicts the results of a comparison between raw Capsul starch and three different samples pressure treated at 60 psi/1 pass; 90 psi/1 pass and 90 psi/5 passes. The graph illustrates that the fastest dissolution time occurred for the raw starch/acetaminophen tablet. The lowest dissolution profile occurred with the 90 psi/1 pass treated starch; the other two samples possess altered dissolution profiles.

Additional tableting studies were conducted using Vitamin C and

Acetaminophen active agents. Table I, below, indicates the composition of the tablets formed. Table II depicts the physical properties of the formulated tablets. Note the extreme hardness provided by the pressure treated starch sample which is identified as "Delta starch" as compared to microcrystalline cellulose (Avicel 101). The particular starch used was pressure treated at 90 psi/1 pass according to the method Experiment 1. Also note that the treated starch tablets exhibit a superior appearance with no chipping defects.

TABLE I

Tablet Formulations

| FAA0309 | | FAA0309A | |
| --- | --- | --- | --- |
| Ascorbic Acid | 255 mg | Ascorbic Acid | 255 mg |
| Avicel 101 | 159 mg | D-Starch | 159 mg |
| Stearic Acid | 12 mg | Stearic Acid | 12 mg |
| Aerosil 200 | 2 mg | Aerosil 200 | 2 mg |
| Tablet Weight | 428 mg | Tablet Weight | 428 mg |
| FAP0309A | | FAP0309B | |
| Acetaminophen | 150 mg | Acetaminophen | 150 mg |
| Avicel 101 | 264 mg | D-Starch | 264 mg |
| Stearic Acid | 12 mg | Stearic Acid | 12 mg |
| Aerosil 200 | 2 mg | Aerosil 200 | 2 mg |
| Tablet Weight | 428 mg | Tablet Weight | 428 mg |

TABLE 11

Physical Properties of Tablets

| Formula | Weight*** | Thickness** | Hardness | Friability | Disintegration** |
| --- | --- | --- | --- | --- | --- |
| FAA0309 | 440 mg | 0.251" | 9.14 SC | −0.45%* | Less than 60 Seconds |
| FAA0309A | 420 mg | 0.257" | 20.60 SC | −0.72% | 9 Minutes |
| FAP0309A | 431 mg | 0.250" | 13.76 SC | −2.21%* | Less than 60 Seconds |
| FAP0309B | 436 mg | 0.291" | 36.77 SC | −0.00% | 50% Weight Loss at 10 Minutes |

*Corner chipping observed
**Average of three readings
***Average of ten tablets

Tablets were then tested for disintegration properties. In each of the microcrystalline cellulose tablets, disintegration occurred in less than 60 seconds. The pressure treated starch tablets, on the other hand, required 9 to 10 minutes indicating a much slower release profile, In the case of acetaminophen, which is used often as headache remedy, faster release is desired. This may be accomplished by adding disintegration enhancers to the tablet formula such as, for example, sodium bicarbonate.

Table III, below, shows the hardness of vitamin C (ascorbic acid) tablets made using microcrystalline cellulose and pressure treated "Delta" starch, respectively, Again, the starch used was treated at 90 psi/1 pass and the formulations used for the tablet corresponded to those depicted in Table II, above. As predicted, hardness profiles similar to those described above were realized.

TABLE III

Compressibility Profiles of Ascorbic Acid Tablets Prepared with D-Starch and Avicel 101

| Formula # | Pressure | Hardness | Appearance |
|---|---|---|---|
| FAA0309 | Low | 3.95 SC | Smooth Surface, Slightly Shiny |
|  | Optimum | 9.14 SC | Smooth Surface, Shiny |
|  | High | 19.60 SC | Smooth Surface, Shiny |
| FAA0309A | Low | 0.00 SC | Rough Surface, Dull |
|  | Optimum | 5.04 SC | Rough Surface, Dull |
|  | High | 21.63 SC | Smooth Surface, Slightly Shiny |
|  | Optimum/High | 20.59 SC | Smooth Surface, Slightly Shiny |

EXAMPLE 4

Acacia gum, also known as gum arabic, was treated according to the same methods employed on starch as described in Example 1. The acacia gum was purchased from TIC Gums, Inc.

Figure 11A:
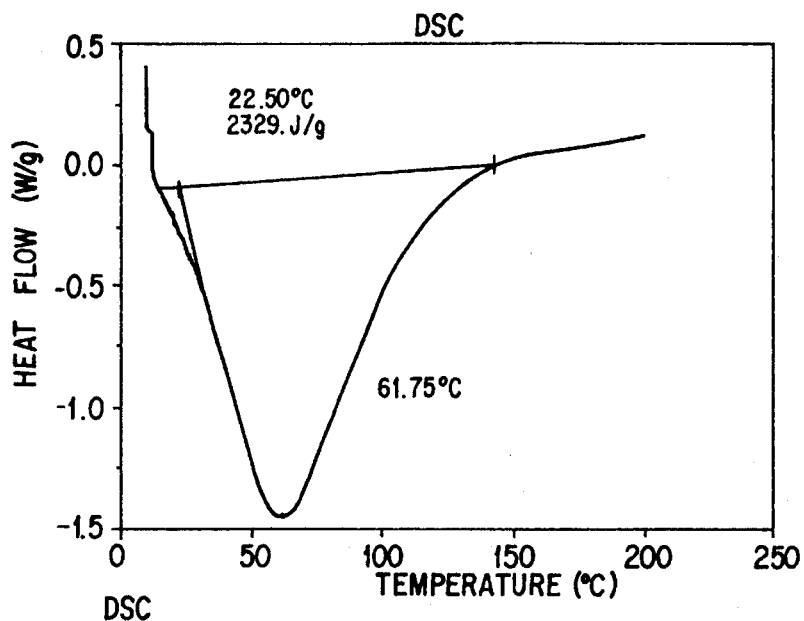
FIGS. 11A through 11C are illustrations of the two basic components of starch, amylose and amylopectin, along with a table indicating the various types of starches available and their technical features.
Figure 11B:
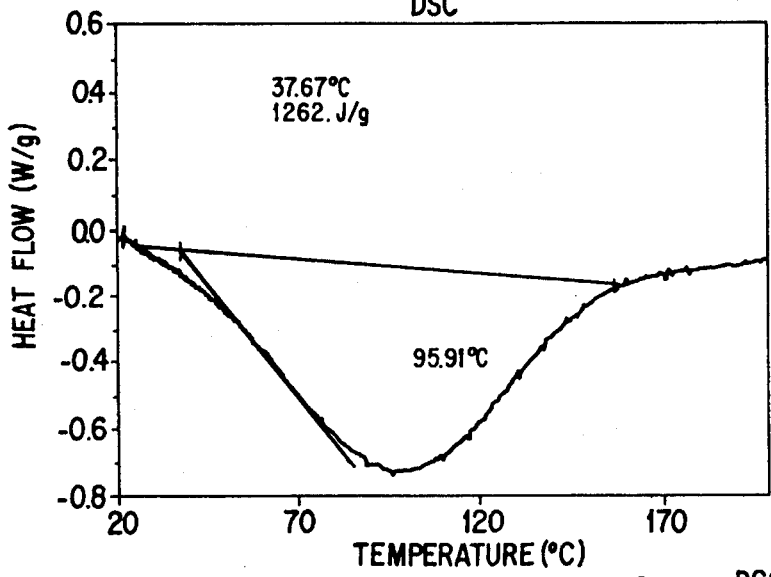
Figure 11C:
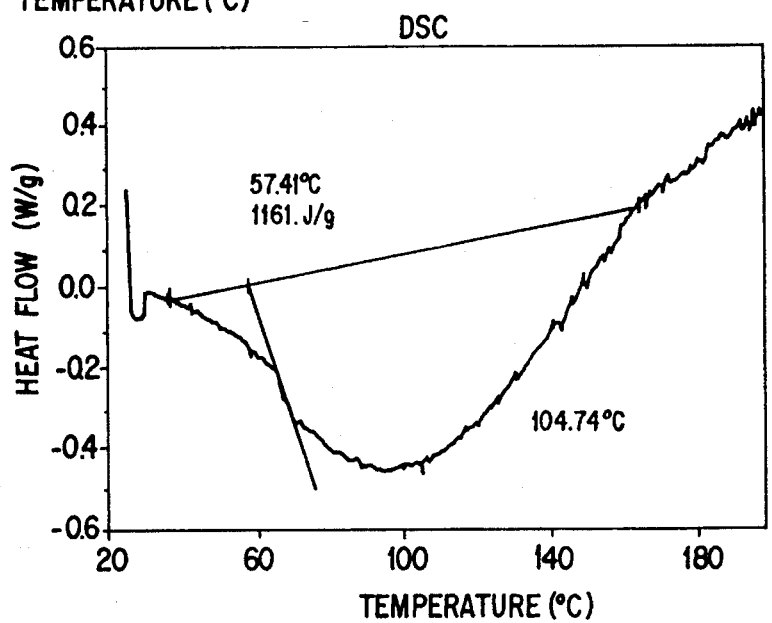

FIGS. 11A–C are the DSC spectra of the various samples of gum arabic treated, FIG. 11A results from the raw gum arabic as received from the supplier. FIG. 11B results from gum arabic treated at 60 psi/5 passes. FIG. 11C results from gum arabic treated at 90 psi/5 passes.

Referring to FIG. 11A it can be seen that an endothermy exists at 61.75° C. for the raw untreated gum arabic. FIG. 11B reveals an endothermy increase to 95.91° C., a difference of 34.16° C. This figure represents the gain in the temperature starting point for decomposition. FIG. 11C reveals an increase in the starting point of decomposition depicted at 104.74° C.

A comparison of the decomposition starting points for all three gum arabic samples shows that the 60 psi/5 pass pressure treated sample had a gain of 34.16° C. whereas the 90 psi/5 pass sample had a gain over the 60 psi/5 pass sample of 8.8° C. and a very significant gain of 42.99° C. over the control sample. The 90 psi/5 pass sample thus realized a thermal stability modification enabling it to withstand 58.95% more thermal energy before the onset of decomposition than can the untreated acacia.

Figure 12:
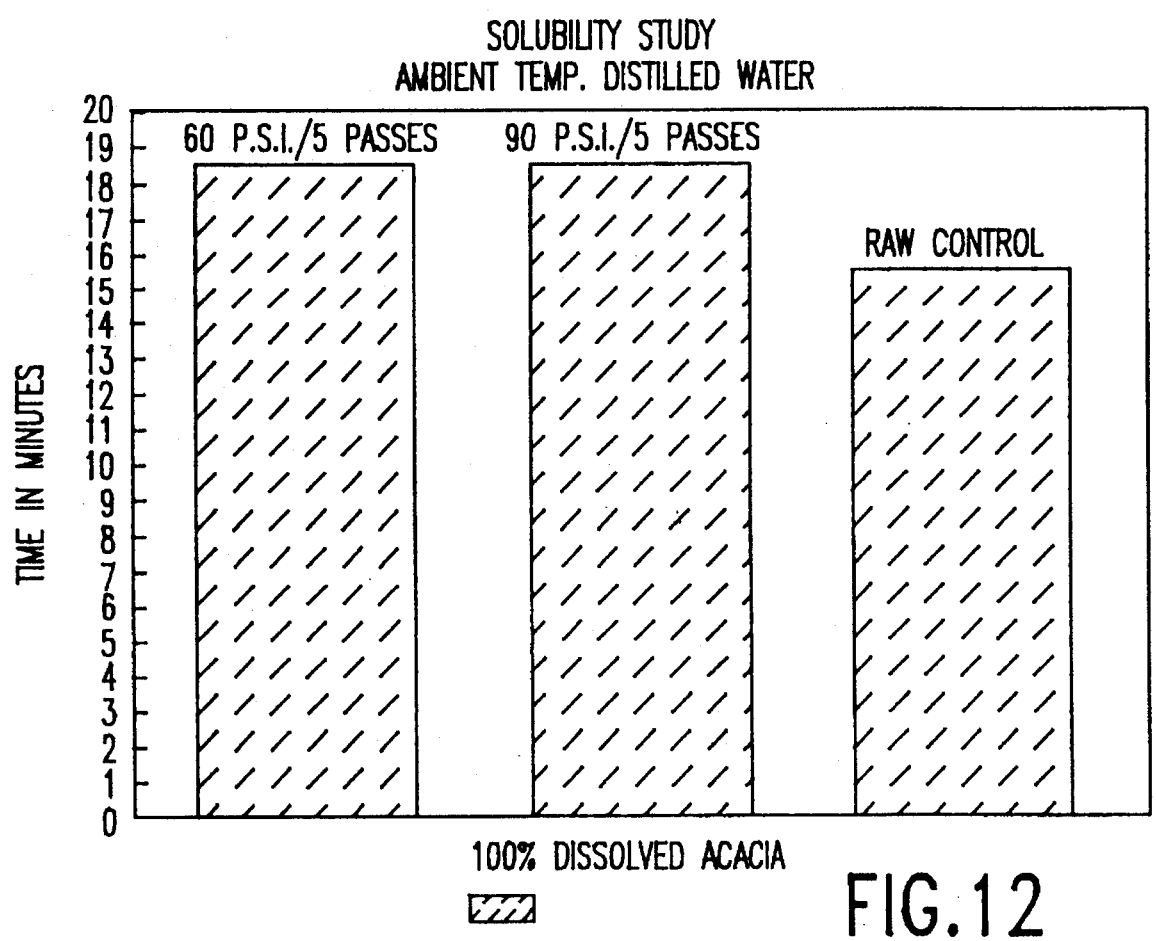
FIGS. 12, 13 and 14 ere graphs showing the results of comparative dissolution studies under several different test conditions.
Figure 13:
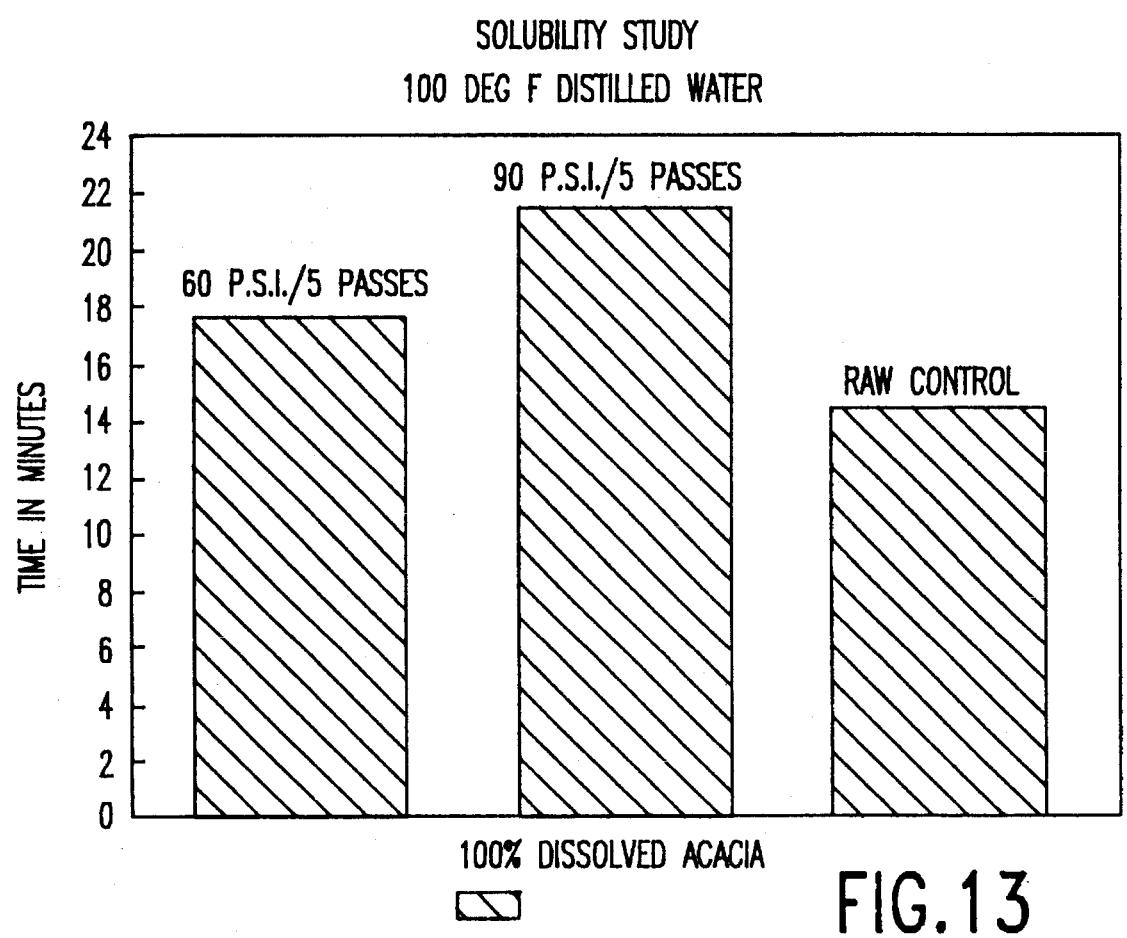
Figure 14:
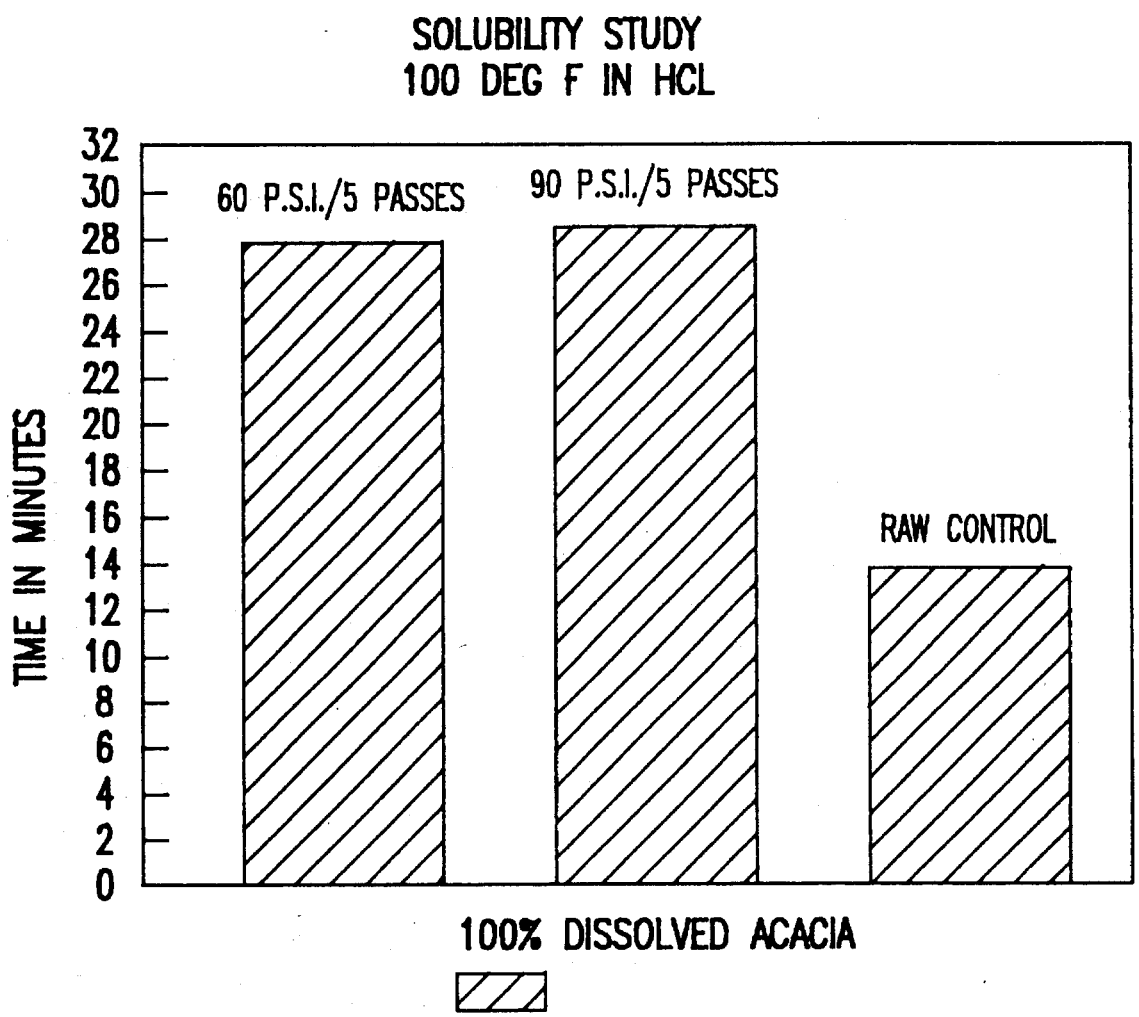

A dissolution study was also performed the results of which are illustrated in the graphs of FIGS. 12, 13 and 14. Referring to FIG. 12 it can be observed that both pressure treated samples exhibited slower dissolution rates in ambient distilled water than did untreated sample. There was little difference between the averaged 60 psi and 90 psi samples. FIG. 13 reveals a greater difference between the two pressure settings, when subjected to 100° F. distilled water. In both cases the pressure treated samples dissolved at a slower rate compared to the raw sample. Finally, FIG. 14 reveals the dissolution profile of all samples in 1 Normal HCL solution at 100° F. Again, the pressure treated samples exhibit slower dissolution rates compared with the untreated samples.

The following table summarizes the general results observed for the Gum Arabic samples:

TABLE IV

Gum Arabic Comparisons

| Average | Dissolution Times* | | | Note |
|---|---|---|---|---|
|  | Sample #5 60 psi | Sample #6 90 psi | Sample #7 Raw Control |  |
| Average of 5 Runs | 18:51 | 18:49 | 15:40 | Room Temp. $H_2O$ |
| Average of 5 Runs | 17:41 | 21:52 | 14:01 | 100° F. $H_2O$ |
| Average of 5 Runs | 27:56 | 28:51 | 14:38 | 1N HCL 100° F. |

*Dissolution time given for sample to totally dissolve in minutes and seconds.

From the above examples and associated experimental results it can be appreciated that other physical properties of starches and acacia gum may also be modified via the subject pressure processing techniques. Additionally, it should be further appreciated that the subject method and apparatus may be employed to impart modified physical properties unto other substrate compositions or combinations thereof, as well.

Thus, it should be understood that the examples described herein are merely illustrative and not intended to limit the invention's ability to modify the structure and physical properties of other polymers such as those referenced in the following tables.

TABLE V

Partial List of Starches

Potato
Tapioca
Corn
Waxy Maize
Wheat
Rice
Amycomaize
Pre-Gelatinize Starches
Starches of Varying Amylose and Amylopectin Ratios
Modified Starches
Genetically Engineered Starches

TABLE VI

Partial List of Natural Polymers

| Carboxymethylcellulose | Cellulose Acetate Phthalate |
|---|---|
| Ethylcellulose | Gelatin |
| Gum Arabic | Starch |
| Bark | Methylcellulose |
| Arabinogelactan | Zein |
| Nitrocellulose | Propylhydroxylcellulose |
| Shellac | Succinylated Gelatin |
| Waxes, Paraffin | Proteins |
| Kraft Lignin | Natural Rubber |

All other natural polymers listed in: "Polymer Handbook", Second Edition, Editors: Brandrup, Immergut

TABLE VII

Partial List of Synthetic Polymers

| Polyvinyl Alcohol | Polyethylene |
|---|---|
| Polypropylene | Polystyrene |
| Polyacrylamide | Polyether |
| Polester | Polyamide |
| Polyurea | Polyvinyl Acetate |

TABLE VII-continued
Partial List of Synthetic Polymers

| | |
|---|---|
| Ethylene Vinyl Acetate Copolymer | Epoxy |
| Polyvinylidene Chloride | Polyvinyl Chloride |
| Polyacrylate | Polyacrylonitrile |
| Chlorinated Polyethylene | Acetal Copolymer |
| Polyurethane | Polyvinylpyrrolidone |
| Poly (P-Xyllene) | Polymethyl Methacrylate |
| Polyhydroxyethyl Methacrylate | |

All other synthetic polymers listed in: "Polymer Handbook", Second Edition, Editors: Brandrup, Immergut Although the present invention has been described with reference to the particular embodiments herein set forth, it is understood that the present disclosure has been made only by way of example and that numerous changes in details of construction may be resorted to without departing from the spirit and scope of the invention. Thus, the scope of the invention should not be limited by the foregoing specifications, but rather only by the scope of the claims appended hereto.

What is claimed is:

1. A method for modifying the physical properties of a polymer substrate, comprising:
    a. charging the polymer to a chamber wherein it may subjected to an abrupt pressure change; and
    b. subjecting the polymer to an abrupt pressure change through a liquid media,
    said polymer being gum arabic.

* * * * *